US012610970B2

(12) United States Patent
Bostick et al.

(10) Patent No.: US 12,610,970 B2
(45) Date of Patent: *Apr. 28, 2026

---

(54) COMPOSITIONS FOR GUT HEALTH

(71) Applicant: INTERNATIONAL N&H DENMARK APS, Kongens Lyngby (DK)

(72) Inventors: Michael W. Bostick, Wilmington, DE (US); Qiong Cheng, Wilmington, DE (US); John Thomas Gannon, Hockessin, DE (US); Raymond E. Jackson, Newark, DE (US); Victoria Vellejo Kelly, Palo Alto, CA (US); Alexander D Kopatsis, Wilmington, DE (US); Claus Lang, Palo Alto, DE (US); Gerda Saxer Quance, Wilmington, DE (US); Qiong Wang, Palo Alto, DE (US); Julia Yager, Palo Alto, DE (US); Rick W Ye, Wilmington, DE (US)

(73) Assignee: INTERNATIONAL N&H DENMARK APS, Kongens Lyngby (DK)

( * ) Notice: Subject to any disclaimer, the term of this patent is extended or adjusted under 35 U.S.C. 154(b) by 951 days.

This patent is subject to a terminal disclaimer.

(21) Appl. No.: 17/634,818

(22) PCT Filed: Aug. 14, 2020

(86) PCT No.: PCT/US2020/046365
§ 371 (c)(1),
(2) Date: Feb. 11, 2022

(87) PCT Pub. No.: WO2021/034660
PCT Pub. Date: Feb. 25, 2021

(65) Prior Publication Data
US 2022/0330576 A1 Oct. 20, 2022

Related U.S. Application Data

(60) Provisional application No. 62/887,847, filed on Aug. 16, 2019.

(51) Int. Cl.
| | |
|---|---|
| *A23K 10/18* | (2016.01) |
| *A23K 20/158* | (2016.01) |
| *A23K 20/189* | (2016.01) |
| *A23K 50/75* | (2016.01) |
| *A61P 1/00* | (2006.01) |
| *A61P 31/04* | (2006.01) |
| *A61P 43/00* | (2006.01) |

(52) U.S. Cl.
CPC ............ *A23K 10/18* (2016.05); *A23K 20/158* (2016.05); *A23K 20/189* (2016.05); *A23K 50/75* (2016.05); *A61P 1/00* (2018.01); *A61P 31/04* (2018.01); *A61P 43/00* (2018.01); *A23V 2400/173* (2023.08); *A23V 2400/181* (2023.08)

(58) Field of Classification Search
CPC . A23K 10/18; A23K 50/75; A61P 1/00; A61P 31/04; A61P 43/00; A23V 2400/173; A23V 2400/11; A23V 50/70; A23V 2400/181
See application file for complete search history.

(56) References Cited

U.S. PATENT DOCUMENTS

| | | | |
|---|---|---|---|
| 6,287,841 B1 | 9/2001 | Mulleners et al. | |
| 8,101,170 B2 | 1/2012 | Plail et al. | |
| 8,420,074 B2 | 4/2013 | Rehberger et al. | |
| 12,250,956 B2 * | 3/2025 | Gruber .................. A23K 50/75 | |
| 2006/0067924 A1 * | 3/2006 | Lee ..................... G01N 33/5088 | |
| | | | 424/93.45 |
| 2008/0263688 A1 | 10/2008 | Lassen et al. | |
| 2014/0037582 A1 | 2/2014 | Romero et al. | |
| 2015/0118203 A1 * | 4/2015 | Boyette ................ A61K 35/741 | |
| | | | 119/51.01 |
| 2017/0260546 A1 | 9/2017 | Qimron et al. | |
| 2019/0192587 A1 | 6/2019 | Kazemi et al. | |

FOREIGN PATENT DOCUMENTS

| | | |
|---|---|---|
| CN | 103429093 A | 12/2012 |
| CN | 103533843 A | 1/2014 |
| GB | 1011513.7 | 12/1965 |
| RU | 2658978 C1 | 6/2018 |
| WO | 1989/06270 A1 | 7/1989 |
| WO | 1989/06279 A1 | 7/1989 |
| WO | 1992/012645 A1 | 8/1992 |

(Continued)

OTHER PUBLICATIONS

Dhama, K et al. Rotavirus diarrhea in bovines and other domestic animals. Vet. Res. Commun. 2009. 33: 1-23. (Year: 2009).*
Dexian, Z et al. Lactobacillus reuteri ATCC 55730 and L22 display probiotic potential in vitro and protect against *Salmonella*-induced pullorum disease in a chick model of infection. Research in Veterinary Science. 2012. 93: 366-373. (Year: 2012).*
'Application Sequence Alignments with Bauer's Sequences.' OM nucleic-nucleic search. Performed on Mar. 22, 2025. (Year: 2025).*
'SEQ ID No. 9 Search in GenEmbl database.' GenEmbl database. OM nucleic-nucleic search. Performed on Mar. 6, 2025. (Year: 2025).*
'SEQ ID No. 7 Search in GenEmbl database.' GenEmbl database. OM nucleic-nucleic search. Performed on Mar. 6, 2025. (Year: 2025).*

(Continued)

*Primary Examiner* — David W Berke-Schlessel
*Assistant Examiner* — Susan E. Fernandez

(57) ABSTRACT

Provided herein, inter alia, are compositions of organic acid-producing microorganisms and methods of making and using the same to inhibit pathogenic bacterial populations in the gastrointestinal tracts of an animal and additionally promote improvement of one or more metrics in an animal, such as increased bodyweight gain, decreased feed conversion ratio (FCR), improved gut barrier integrity, reduced mortality, reduced pathogen infection, and reduced pathogen shedding in feces.

11 Claims, 1 Drawing Sheet

Specification includes a Sequence Listing.

(56)          References Cited

FOREIGN PATENT DOCUMENTS

| WO | 1992/19729 | A1 | 11/1992 |
| WO | 1994/25583 | A1 | 11/1994 |
| WO | 1997/016076 | A1 | 5/1997 |
| WO | 1998/20115 | A1 | 5/1998 |
| WO | 2004/085638 | A1 | 10/2004 |
| WO | 2006/037327 | A2 | 4/2006 |
| WO | 2006/037328 | A1 | 4/2006 |
| WO | 2006/038062 | A1 | 4/2006 |
| WO | 2006/038128 | A2 | 4/2006 |
| WO | 2006/043178 | A2 | 4/2006 |
| WO | 2007/044968 | A2 | 4/2007 |
| WO | 2007/112739 | A1 | 10/2007 |
| WO | 2008/092901 | A2 | 8/2008 |
| WO | 2008/097619 | A3 | 8/2008 |
| WO | 2009/129489 | A2 | 10/2009 |
| WO | 2010/122532 | A2 | 10/2010 |
| WO | 2011/117396 | A2 | 9/2011 |
| WO | 2012/004759 | A2 | 1/2012 |
| WO | 2012/110766 | A2 | 8/2012 |
| WO | 2016/120405 | A1 | 8/2016 |

OTHER PUBLICATIONS

Greifova, G et al. Analysis of antimicrobial and immunomodulatory substances produced by heterofermentative Lactobacillus reuteri. Folia Microbiol. 2017. 62: 515-524. (Year: 2017).*

Rosander, A et al. Removal of antibiotic resistance gene-carrying plasmids from Lactobacillus reuteri ATCC 55730 and characterization of the resulting daughter strain, L. reuteri DSM 17938. Applied and Environmental Microbiology. 2008. 74(19): 6032-6040. (Year: 2008).*

* cited by examiner

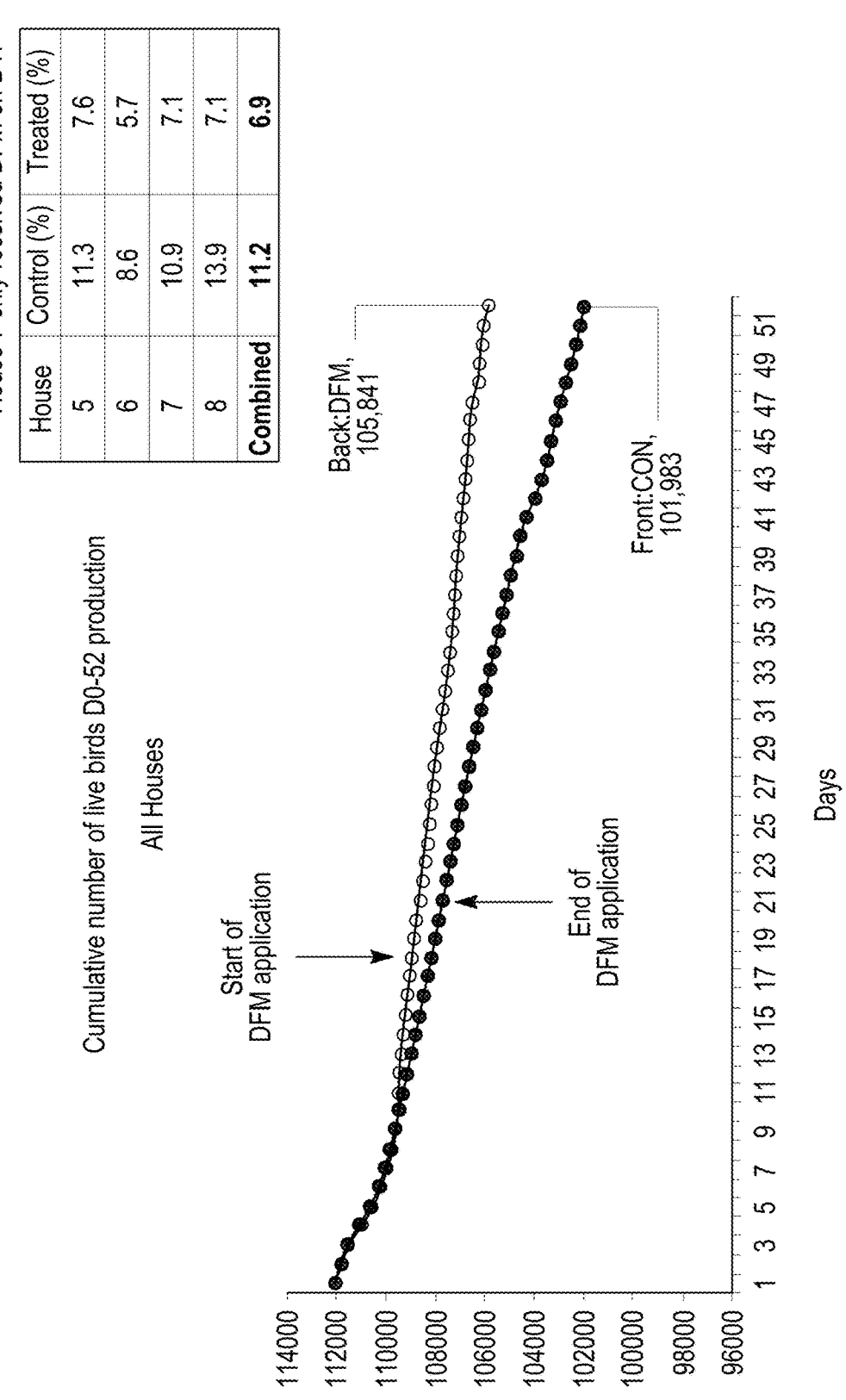

COMPOSITIONS FOR GUT HEALTH

CROSS-REFERENCE TO RELATED APPLICATIONS

This application is a U.S. National Stage Application under 35 U.S.C. § 371 of International Patent Application No. PCT/US2020/046365, filed Aug. 14, 2020, which claims priority to U.S. Provisional Patent Application No. 62/887,847, filed Aug. 16, 2019, the disclosure of each of which is incorporated by reference herein in its entirety.

FIELD OF THE INVENTION

Provided herein, inter alia, are multi-strain direct fed microbial bacterial consortia useful for improving animal gut health and/or performance as well as methods of making and using the same.

INCORPORATION BY REFERENCE TO A SEQUENCE LISTING

The contents of the electronic submission of the text file Sequence Listing, named "20200813_NB41585WOPCT_SequenceList_ST25.txt" _was created on Aug. 13, 2020, and is 24296 bytes in size, which is hereby incorporated by reference in its entirety.

BACKGROUND

In monogastric animal species such as birds, the gastrointestinal tract and intestinal-associated microflora are not only involved in digestion and absorption but also interact with the immune and central nervous system to modulate health. The inside of the intestinal tract is coated with a thin layer of sticky, viscous mucous, and embedded in this mucus layer are millions and millions of bacteria and other microbes. When the intestinal bacteria are in balance (i.e., the good bacteria outnumber the bad bacteria), the gut is said to be healthy. A healthy microbiota provides the host with multiple benefits, including colonization resistance to a broad spectrum of pathogens, essential nutrient biosynthesis and absorption, and immune stimulation that maintains a healthy gut epithelium and an appropriately controlled systemic immunity. In settings of "dysbiosis" or disrupted symbiosis, microbiota functions can be lost or deranged, resulting in increased susceptibility to pathogens, altered metabolic profiles, or induction of proinflammatory signals that can result in local or systemic inflammation or autoimmunity. Thus, the intestinal microbiota of poultry plays a significant role in the pathogenesis of many diseases and disorders, including a variety of pathogenic infections of the gut such as coccidiosis or necrotic enteritis.

Over the past several years, there has been increasing governmental and consumer pressure applied to the animal feed industry to decrease or curtail the use of antibiotics as components of animal nutrition feeding regimens. This pressure is due in large part to the recognition that use of such antibiotics contribute to the rise of antibiotic-resistant pathogenic microorganisms. However, this "No Antibiotics Ever" consumer trend, especially in the poultry industry, has led to the re-emergence of bacterial diseases, particularly necrotic enteritis (*Poultry Science*, Volume 97, Issue 6, 1 Jun. 2018, 1929-1933). Necrotic enteritis is caused by certain toxin-producing *Clostridium perfringens* strains. Under certain conditions *C. perfringens* produces toxins which cause lesions in the small intestines and ultimately result in reduced growth or death of the infected birds. Accordingly, there is currently a recognized need for products and methods capable of reducing pathogenic bacterial populations in the digestive tracts of domesticated animals such as birds without the use of traditionally-used antibiotics.

The subject matter disclosed herein addresses these needs and provides additional benefits as well.

SUMMARY

Provided herein, inter alia, are multi-strain direct fed microbial bacterial consortia of organic acid-producing microorganisms and methods of making and using the same to inhibit pathogenic bacterial populations in the gastrointestinal tracts of an animal (such as birds, for example, chickens) and additionally promote improvement of one or more metrics in an animal such as increased bodyweight gain, decreased feed conversion ratio (FCR), improved gut barrier integrity, reduced mortality, reduced pathogen infection, and reduced pathogen shedding in feces.

Accordingly, in some aspects, provided herein is a feed additive composition comprising a direct fed microbial (DFM) comprising (a) at least one biologically pure strain of (i) *Lactobacillus reuteri*; and/or (ii) *L. salivarius*; and (b) one or more additional biologically pure strain(s) of (i) *L. reuteri*; (ii) *L. agilis*; (iii) *L. crispatus*; and/or (iv) *L. gallinarum*. In some embodiments, the feed additive composition comprises three biologically pure strains of *L. reuteri*. In some embodiments of any of the embodiments provided herein, the feed additive composition comprises (a) a bacterial strain having a 16S ribosomal RNA sequence displaying at least 97.0% sequence similarity to a 16S ribosomal RNA sequence of a *L. reuteri* strain S1 deposited at Westerdijk Fungal Biodiversity Institute (WFDB) under number CBS 145921; and (b)(i) a bacterial strain having a 16S ribosomal RNA sequence displaying at least 97.0% sequence similarity to a 16S ribosomal RNA sequence of a *L. reuteri* strain S2 deposited at WFDB under number CBS 145922; and (ii) a bacterial strain having a 16S ribosomal RNA sequence displaying at least 97.0% sequence similarity to a 16S ribosomal RNA sequence of a *L. reuteri* strain S3 deposited at WFDB under number CBS 145923. In some embodiments of any of the embodiments provided herein, the composition comprises (a) *L. reuteri* strain S1 (CBS 145921) or a live strain having all of the identifying characteristics of *L. reuteri* strain S1 (CBS 145921); and (b)(i) *L. reuteri* strain S2 (CBS 145922) or a live strain having all of the identifying characteristics of *L. reuteri* strain S2 (CBS 145922); and (ii) *L. reuteri* strain S3 (CBS 145923) or a live strain having all of the identifying characteristics of *L. reuteri* strain S3 (CBS 145923) either (A) alone; or (B) in combination with a culture supernatant derived from each of these strains. In some embodiments, the feed additive composition comprises (a) a biologically pure strain of *L. salivarius*; and (b)(i) a biologically pure strain of *L. gallinarum*; and (ii)(A) a biologically pure strain of *L. agilis*; or (B) a biologically pure strain of *L. reuteri*. In some embodiments of any of the embodiments provided herein, the feed additive composition comprises (a) a bacterial strain having a 16S ribosomal RNA sequence displaying at least 97.0% sequence similarity to a 16S ribosomal RNA sequence of a *L. salivarius* strain H2 deposited at WFDB under number CBS 145919; and (b)(i) a bacterial strain having a 16S ribosomal RNA sequence displaying at least 97.0% sequence similarity to a 16S ribosomal RNA sequence of a *L. gallinarum* strain H1 deposited at WFDB under number CBS 145918; and (ii)(A) a bacterial strain having a 16S ribosomal RNA sequence displaying at least 97.0% sequence similarity to a 16S ribosomal RNA sequence of an *L. agilis* strain H3 comprising SEQ ID NO: 1; or (B) a bacterial strain having a 16S ribosomal RNA sequence displaying at least 97.0% sequence similarity to a 16S ribosomal RNA sequence of an *L. reuteri* strain A2 deposited at WFDB under number CBS 145924. In some embodiments, the composition comprises (a) *L. salivarius* strain H2 (CBS 145919) or a live strain having all of the identifying characteristics of *L. salivarius* strain H2 (CBS 145919); and (b)(i) *L. gallinarum* strain H1 (CBS 145918) or a live strain having all of the identifying characteristics of *L. gallinarum* strain H1 (CBS 145918); and (ii) *L. reuteri* strain A2 (CBS 145924) or a live strain having all of the identifying characteristics of *L. reuteri* strain A2 (CBS 145924) either (A) alone; or (B) in combination with a culture supernatant derived from each of these strains. In some embodiments, the feed additive composition comprises (a) a biologically pure strain of *L. salivarius*; and (b)(i) a biologically pure strain of *L. agilis*; and a biologically pure strain of *L. reuteri*. In some embodiments of any of the embodiments provided herein, the feed additive composition comprises (a) a bacterial strain having a 16S ribosomal RNA sequence displaying at least 97.0% sequence similarity to a 16S ribosomal RNA sequence of an *L. salivarius* strain A1 comprising SEQ ID NO: 2; and (b)(i) a bacterial strain having a 16S ribosomal RNA sequence displaying at least 97.0% sequence similarity to a 16S ribosomal RNA sequence of an *L. agilis* strain A3 comprising SEQ ID NO: 3; and (ii) a bacterial strain having a 16S ribosomal RNA sequence displaying at least 97.0% sequence similarity to a 16S ribosomal RNA sequence of an *L. reuteri* strain A2 deposited at WFDB under number CBS 145924 either (A) alone; or (B) in combination with a culture supernatant derived from each of these strains. The feed additive composition of claim 9, comprising *L. reuteri* strain A2 (CBS 145924) or a live strain having all of the identifying characteristics of *L. reuteri* strain A2 (CBS 145924). The feed additive composition of claim 1, comprising (a) a biologically pure strain of *L. salivarius*; and (b)(i) a biologically pure strain of *L. agilis*; and (ii) a biologically pure strain of *L. crispatus*. In some embodiments of any of the embodiments provided herein, the feed additive composition comprises (a) a bacterial strain having a 16S ribosomal RNA sequence displaying at least 97.0% sequence similarity to a 16S ribosomal RNA sequence of an *L. salivarius* strain D2 comprising SEQ ID NO: 4; (b)(i) a bacterial strain having a 16S ribosomal RNA sequence displaying at least 97.0% sequence similarity to a 16S ribosomal RNA sequence of an *L. agilis* strain D1 comprising SEQ ID NO: 5; and (ii) a bacterial strain having a 16S ribosomal RNA sequence displaying at least 97.0% sequence similarity to a 16S ribosomal RNA sequence of an *L. crispatus* strain D3 comprising SEQ ID NO: 6 either (A) alone; or (B) in combination with a culture supernatant derived from each of these strains. In some embodiments of any of the embodiments provided herein, a) the 16S ribosomal RNA sequence of *L. reuteri* strain S1 comprises the nucleotide sequence of SEQ ID NO: 7; and (b)(i) the 16S ribosomal RNA sequence of *L. reuteri* strain S2 comprises the nucleotide sequence of SEQ ID NO: 8; and (ii) the 16S ribosomal RNA sequence of *L. reuteri* strain S3 comprises the nucleotide sequence of SEQ ID NO: 9. In some embodiments of any of the embodiments provided herein, a) the 16S ribosomal RNA sequence of *L. salivarius* strain H2 comprises the nucleotide sequence of SEQ ID NO: 10; and (b)(i) the 16S ribosomal RNA sequence of *L. gallinarum* strain H1 comprises the nucleotide sequence of SEQ ID NO: 11; and (ii) the 16S ribosomal RNA sequence of *L. reuteri* strain A2 comprises the nucleotide sequence of SEQ ID NO: 12. In some embodiments, (b)(ii) the 16S ribosomal RNA sequence of *L. reuteri* strain A2 comprises the nucleotide sequence of SEQ ID NO: 12. In some embodiments of any of the embodiments provided herein, said one or more strains further comprise one or more inactivated or deleted antimicrobial resistance (AMR) genes. In some embodiments of any of the embodiments provided herein, the composition produces one or more organic acids selected from the group consisting of lactate, butyrate, isobutyrate, propionate, acetate, isovalerate, and valerate. In some embodiments of any of the embodiments provided herein, the composition further comprises one or more enzymes. In some embodiments, the one or more enzymes are selected from the group consisting of a phytase, a protease, an amylase, a xylanase, and a beta-glucanase. In some embodiments of any of the embodiments provided herein, the composition further comprises one or more essential oils. In some embodiments of any of the embodiments provided herein, each strain is present at a concentration of at least about $1 \times 10^3$ CFU/g feed additive composition to at least about $1 \times 10^9$ CFU/g (such as about $1 \times 10^{15}$ CFU/g) feed additive composition. In some embodiments of any of the embodiments provided herein, the composition inhibits at least one pathogen selected from avian pathogenic *Salmonella* sp., *Escherichia coli*, Clostridion *perfringens* and Enterobacteriaceae in a gastrointestinal tract of a bird having ingested an effective amount of said direct fed microbial composition. In some embodiments of any of the embodiments provided herein, the composition is formulated for delivery to an animal via waterline.

In other aspects, provided herein is a bacterial consortium comprising (a) a bacterial strain having a 16S ribosomal RNA sequence displaying at least 97.0% sequence similarity to a 16S ribosomal RNA sequence of a *L. reuteri* strain S1 deposited at Westerdijk Fungal Biodiversity Institute (WFDB) under number CBS 145921; and (b) a bacterial strain having a 16S ribosomal RNA sequence displaying at least 97.0% sequence similarity to a 16S ribosomal RNA sequence of a *L. reuteri* strain S2 deposited at WFDB under number CBS 145922; and (c) a bacterial strain having a 16S ribosomal RNA sequence displaying at least 97.0% sequence similarity to a 16S ribosomal RNA sequence of a *L. reuteri* strain S3 deposited at WFDB under number CBS 145923. In some embodiments, the consortium comprises (a) *L. reuteri* strain S1 (CBS 145921) or a live strain having all of the identifying characteristics of *L. reuteri* strain S1 (CBS 145921); and (b) *L. reuteri* strain S2 (CBS 145922) or a live strain having all of the identifying characteristics of *L. reuteri* strain S2 (CBS 145922); and (c) *L. reuteri* strain S3 (CBS 145923) or a live strain having all of the identifying characteristics of *L. reuteri* strain S3 (CBS 145923) either (A) alone; or (B) in combination with a culture supernatant derived from each of these strains. In some embodiments, the consortium comprises a) the 16S ribosomal RNA sequence of *L. reuteri* strain S1 comprises the nucleotide sequence of SEQ ID NO: 7; and (b) the 16S ribosomal RNA sequence of *L. reuteri* strain S2 comprises the nucleotide sequence of SEQ ID NO: 8; and (c) the 16S ribosomal RNA sequence of *L. reuteri* strain S3 comprises the nucleotide sequence of SEQ ID NO: 9. In some embodiments of any of the embodiments disclosed herein, one or more bacterial strains further comprise one or more inactivated or deleted Antimicrobial resistance (AMR) genes. In some embodiments of any of the embodiments disclosed herein, the consortium produces one or more organic acids selected from the group consisting of lactate, butyrate, isobutyrate, propionate, acetate, isovalerate, and valerate. In some embodiments of any of the embodiments disclosed herein, each strain is present at a concentration of at least about $1\times10^3$ CFU/animal/day to at least about $1\times10^{15}$ CFU/animal/day in the consortium. In some embodiments of any of the embodiments disclosed herein, the consortium inhibits at least one pathogen selected from avian pathogenic *Salmonella* sp., *Escherichia coli, Clostridium perfringens* and Enterobacteriaceae in a gastrointestinal tract of a bird having ingested an effective amount of said direct fed microbial composition.

In further aspects, provided herein is a bacterial consortium comprising (a) a bacterial strain having a 16S ribosomal RNA sequence displaying at least 97.0% sequence similarity to a 16S ribosomal RNA sequence of a *L. salivarius* strain H2 deposited at WFDB under number CBS 145919; and (b) a bacterial strain having a 16S ribosomal RNA sequence displaying at least 97.0% sequence similarity to a 16S ribosomal RNA sequence of a *L. gallinarum* strain H1 deposited at WFDB under number CBS 145918; and (c)(i) a bacterial strain having a 16S ribosomal RNA sequence displaying at least 97.0% sequence similarity to a 16S ribosomal RNA sequence of an *L. agilis* strain H3 comprising SEQ ID NO: 1; or (ii) a bacterial strain having a 16S ribosomal RNA sequence displaying at least 97.0% sequence similarity to a 16S ribosomal RNA sequence of an *L. reuteri* strain A2 deposited at WFDB under number CBS 145924. In some embodiments, the consortium comprises (a) *L. salivarius* strain H2 (CBS 145919) or a live strain having all of the identifying characteristics of *L. salivarius* strain H2 (CBS 145919); and (b) *L. gallinarum* strain H1 (CBS 145918) or a live strain having all of the identifying characteristics of *L. gallinarum* strain H1 (CBS 145918); and (c) *L. reuteri* strain A2 (CBS 145924) or a live strain having all of the identifying characteristics of *L. reuteri* strain A2 (CBS 145924) either (A) alone; or (B) in combination with a culture supernatant derived from each of these strains. In some embodiments of any of the embodiments disclosed herein, one or more bacterial strains further comprise one or more inactivated or deleted Antimicrobial resistance (AMR) genes. In some embodiments of any of the embodiments disclosed herein, the consortium produces one or more organic acids selected from the group consisting of lactate, butyrate, isobutyrate, propionate, acetate, isovalerate, and valerate. In some embodiments of any of the embodiments disclosed herein, each strain is present at a concentration of at least about $1\times10^3$ CFU/animal/day to at least about $1\times10^{15}$ CFU/animal/day in the consortium. In some embodiments of any of the embodiments disclosed herein, the consortium inhibits at least one pathogen selected from avian pathogenic *Salmonella* sp., *Escherichia coli, Clostridium perfringens* and Enterobacteriaceae in a gastrointestinal tract of a bird having ingested an effective amount of said direct fed microbial composition.

In still additional aspects, provided herein is a bacterial consortium comprising (a) a bacterial strain having a 16S ribosomal RNA sequence displaying at least 97.0% sequence similarity to a 16S ribosomal RNA sequence of an *L. salivarius* strain A1 comprising SEQ ID NO: 2; and (b) a bacterial strain having a 16S ribosomal RNA sequence displaying at least 97.0% sequence similarity to a 16S ribosomal RNA sequence of an *L. agilis* strain A3 comprising SEQ ID NO: 3; and (c) a bacterial strain having a 16S ribosomal RNA sequence displaying at least 97.0% sequence similarity to a 16S ribosomal RNA sequence of an

*L. reuteri* strain A2 deposited at WFDB under number CBS 145924 either (A) alone; or (B) in combination with a culture supernatant derived from each of these strains. In some embodiments, the consortium comprises *L. reuteri* strain A2 (CBS 145924) or a live strain having all of the identifying characteristics of *L. reuteri* strain A2 (CBS 145924). In some embodiments of any of the embodiments disclosed herein, one or more bacterial strains further comprise one or more inactivated or deleted Antimicrobial resistance (AMR) genes. In some embodiments of any of the embodiments disclosed herein, the consortium produces one or more organic acids selected from the group consisting of lactate, butyrate, isobutyrate, propionate, acetate, isovalerate, and valerate. In some embodiments of any of the embodiments disclosed herein, each strain is present at a concentration of at least about $1\times10^3$ CFU/animal/day to at least about $1\times10^{15}$ CFU/animal/day in the consortium. In some embodiments of any of the embodiments disclosed herein, the consortium inhibits at least one pathogen selected from avian pathogenic *Salmonella* sp., *Escherichia coli, Clostridium perfringens* and Enterobacteriaceae in a gastrointestinal tract of a bird having ingested an effective amount of said direct fed microbial composition.

In another aspect, provided herein is a bacterial consortium comprising (a) a bacterial strain having a 16S ribosomal RNA sequence displaying at least 97.0% sequence similarity to a 16S ribosomal RNA sequence of an *L. salivarius* strain D2 comprising SEQ ID NO: 4; (b) a bacterial strain having a 16S ribosomal RNA sequence displaying at least 97.0% sequence similarity to a 16S ribosomal RNA sequence of an *L. agilis* strain D1 comprising SEQ ID NO: 5; and (c) a bacterial strain having a 16S ribosomal RNA sequence displaying at least 97.0% sequence similarity to a 16S ribosomal RNA sequence of an *L. crispatus* strain D3 comprising SEQ ID NO: 6 either (A) alone; or (B) in combination with a culture supernatant derived from each of these strains. In some embodiments of any of the embodiments disclosed herein, one or more bacterial strains further comprise one or more inactivated or deleted Antimicrobial resistance (AMR) genes. In some embodiments of any of the embodiments disclosed herein, the consortium produces one or more organic acids selected from the group consisting of lactate, butyrate, isobutyrate, propionate, acetate, isovalerate, and valerate. In some embodiments of any of the embodiments disclosed herein, each strain is present at a concentration of at least about $1\times10^3$ CFU/animal/day to at least about $1\times10^{15}$ CFU/animal/day in the consortium. In some embodiments of any of the embodiments disclosed herein, the consortium inhibits at least one pathogen selected from avian pathogenic *Salmonella* sp., *Escherichia coli, Clostridium perfringens* and Enterobacteriaceae in a gastrointestinal tract of a bird having ingested an effective amount of said direct fed microbial composition.

In other aspects, provided herein is a premix comprising any of the feed additive compositions disclosed herein or any of the bacterial consortia disclosed herein and at least one mineral and/or at least one vitamin.

In additional aspects, provided herein is a feed comprising any of the feed additive compositions disclosed herein or any of the premixes disclosed herein or any of the bacterial consortia disclosed herein.

In yet other aspects, provided herein is a kit comprising a) any of the feed additive compositions disclosed herein or any of the bacterial consortia disclosed herein; and b) written instructions for administration to an animal. In some embodiments, the kit further comprises one or more enzymes. In some embodiments, the one or more enzymes are selected from the group consisting of a phytase, a protease, an amylase, a xylanase and a beta-glucanase.

In another aspect, provided herein is a method for improving one or more metrics in an animal selected from the group consisting of increased bodyweight gain, intestinal health status, decreased feed conversion ratio (FCR), improved gut barrier integrity, reduced mortality, reduced pathogen infection, and reduced pathogen shedding in feces comprising administering an effective amount of any of the bacterial consortia disclosed herein, or any of the feed additive compositions disclosed herein, any of the premixes disclosed herein, or any of the feeds disclosed herein, thereby improving the one or more metrics in the animal. In some embodiments, the feed additive composition increases one or more of the lactate, acetate, isobutyrate, butyrate, isovalerate, and/or valerate content of the gastrointestinal tract of the animal. In some embodiments of any of the embodiments provided herein, the pathogen is one or more of *Clostridium perfringens, Campylobacter jejuni,* Enterobacteriaceae, a Salmonela sp., and/or *Escherichia coli.* In some embodiments of any of the embodiments provided herein, the method further treats, prevents, or decreases incidence of necrotic enteritis. In some embodiments of any of the embodiments provided herein, the animal is a domesticated bird. In some embodiments, the domesticated bird is selected from the group consisting of chickens, turkeys, ducks, geese, quail, emus, ostriches, and pheasant. In some embodiments, the chicken is a broiler or a layer.

In still further aspects, provided herein is a method for preparing a feed additive composition or a bacterial consortium comprising combining (a) a bacterial strain having a 16S ribosomal RNA sequence displaying at least 97.0% sequence similarity to a 16S ribosomal RNA sequence of a *L. reuteri* strain S1 deposited at Westerdijk Fungal Biodiversity Institute (WFDB) under number CBS 145921; and (b)(i) a bacterial strain having a 16S ribosomal RNA sequence displaying at least 97.0% sequence similarity to a 16S ribosomal RNA sequence of a *L. reuteri* strain S2 deposited at WFDB under number CBS 145922; and (ii) a bacterial strain having a 16S ribosomal RNA sequence displaying at least 97.0% sequence similarity to a 16S ribosomal RNA sequence of a *L. reuteri* strain S3 deposited at WFDB under number CBS 145923. In some embodiments, (a) the *L. reuteri* strain S1 is a *L. reuteri* strain S1 (CBS 145921) or a live strain having all of the identifying characteristics of *L. reuteri* strain S1 (CBS 145921); and (b)(i) the *L. reuteri* strain S2 is a *L. reuteri* strain S2 (CBS 145922) or a live strain having all of the identifying characteristics of *L. reuteri* strain S2 (CBS 145922); and (ii) the *L. reuteri* strain S3 is a *L. reuteri* strain S3 (CBS 145923) or a live strain having all of the identifying characteristics of *L. reuteri* strain S3 (CBS 145923) either (A) alone; or (B) in combination with a culture supernatant derived from each of these strains. In some embodiments of any of the embodiments disclosed herein, the method further comprises combining one or more enzyme(s) with the feed additive composition. In some embodiments, the one or more enzymes are selected from the group consisting of a phytase, a protease, an amylase, a xylanase and a beta-glucanase. In some embodiments of any of the embodiments disclosed herein, at least about $1 \times 10^3$ CFU/g feed additive composition to at least about $1 \times 10^9$ CFU/g feed additive composition is combined to form the feed additive composition. In some embodiments of any of the embodiments disclosed herein, the method further comprises packaging the feed additive composition.

In another aspect, provided herein is a method for preparing a feed additive composition or a bacterial consortium comprising combining (a) a bacterial strain having a 16S ribosomal RNA sequence displaying at least 97.0% sequence similarity to a 16S ribosomal RNA sequence of a *L. salivarius* strain H2 deposited at WFDB under number CBS 145919; and (b)(i) a bacterial strain having a 16S ribosomal RNA sequence displaying at least 97.0% sequence similarity to a 16S ribosomal RNA sequence of a *L. gallinarum* strain H1 deposited at WFDB under number CBS 145918; and (ii)(A) a bacterial strain having a 16S ribosomal RNA sequence displaying at least 97.0% sequence similarity to a 16S ribosomal RNA sequence of an *L. agilis* strain H3 comprising SEQ ID NO: 1; or (B) a bacterial strain having a 16S ribosomal RNA sequence displaying at least 97.0% sequence similarity to a 16S ribosomal RNA sequence of an *L. reuteri* strain A2 deposited at WFDB under number CBS 145924. In some embodiments, (a) the *L. salivarius* strain H2 is an *L. salivarius* strain H2 (CBS 145919) or a live strain having all of the identifying characteristics of *L. salivarius* strain H2 (CBS 145919); and (b)(i) the *L. gallinarum* strain H1 is an *L. gallinarum* strain H1 (CBS 145918) or a live strain having all of the identifying characteristics of *L. gallinarum* strain H1 (CBS 145918); and (ii) the *L. reuteri* strain A2 is an *L. reuteri* strain A2 (CBS 145924) or a live strain having all of the identifying characteristics of *L. reuteri* strain A2 (CBS 145924) either (A) alone; or (B) in combination with a culture supernatant derived from each of these strains. In some embodiments of any of the embodiments disclosed herein, the method further comprises combining one or more enzyme(s) with the feed additive composition. In some embodiments, the one or more enzymes are selected from the group consisting of a phytase, a protease, an amylase, a xylanase and a beta-glucanase. In some embodiments of any of the embodiments disclosed herein, at least about $1 \times 10^3$ CFU/g feed additive composition to at least about $1 \times 10^9$ CFU/g feed additive composition is combined to form the feed additive composition. In some embodiments of any of the embodiments disclosed herein, the method further comprises packaging the feed additive composition.

In other aspects, provided herein is a method for preparing a feed additive composition or a bacterial consortium comprising combining (a) a bacterial strain having a 16S ribosomal RNA sequence displaying at least 97.0% sequence similarity to a 16S ribosomal RNA sequence of an *L. salivarius* strain A1 comprising SEQ ID NO: 2; and (b)(i) a bacterial strain having a 16S ribosomal RNA sequence displaying at least 97.0% sequence similarity to a 16S ribosomal RNA sequence of an *L. agilis* strain A3 comprising SEQ ID NO: 3; and (ii) a bacterial strain having a 16S ribosomal RNA sequence displaying at least 97.0% sequence similarity to a 16S ribosomal RNA sequence of an *L. reuteri* strain A2 deposited at WFDB under number CBS 145924 either (A) alone; or (B) in combination with a culture supernatant derived from each of these strains. In some embodiments, the *L. reuteri* strain A2 is a *L. reuteri* strain A2 (CBS 145924) or a live strain having all of the identifying characteristics of *L. reuteri* strain A2 (CBS 145924). In some embodiments of any of the embodiments disclosed herein, the method further comprises combining one or more enzyme(s) with the feed additive composition. In some embodiments, the one or more enzymes are selected from the group consisting of a phytase, a protease, an amylase, a xylanase and a beta-glucanase. In some embodiments of any of the embodiments disclosed herein, at least about $1 \times 10^3$ CFU/g feed additive composition to at least about $1\times10^9$ CFU/g feed additive composition is combined to form the feed additive composition. In some embodiments of any of the embodiments disclosed herein, the method further comprises packaging the feed additive composition.

In further aspects, provided herein is a method for preparing a feed additive composition or a bacterial consortium comprising combining (a) a bacterial strain having a 16S ribosomal RNA sequence displaying at least 97.0% sequence similarity to a 16S ribosomal RNA sequence of an *L. salivarius* strain D2 comprising SEQ ID NO: 4; (b)(i) a bacterial strain having a 16S ribosomal RNA sequence displaying at least 97.0% sequence similarity to a 16S ribosomal RNA sequence of an *L. agilis* strain D1 comprising SEQ ID NO: 5; and (ii) a bacterial strain having a 16S ribosomal RNA sequence displaying at least 97.0% sequence similarity to a 16S ribosomal RNA sequence of an *L. crispatus* strain D3 comprising SEQ ID NO: 6 either (A) alone; or (B) in combination with a culture supernatant derived from each of these strains. In some embodiments of any of the embodiments disclosed herein, the method further comprises combining one or more enzyme(s) with the feed additive composition. In some embodiments, the one or more enzymes are selected from the group consisting of a phytase, a protease, an amylase, a xylanase and a beta-glucanase. In some embodiments of any of the embodiments disclosed herein, at least about $1\times10^3$ CFU/g feed additive composition to at least about $1\times10^9$ CFU/g feed additive composition is combined to form the feed additive composition. In some embodiments of any of the embodiments disclosed herein, the method further comprises packaging the feed additive composition.

In other aspects, provided herein is a method for preparing a premix comprising combining any of the feed additive compositions disclosed herein with at least one mineral and/or at least one vitamin. In some embodiments, the method further comprises packaging the premix.

Each of the aspects and embodiments described herein are capable of being used together, unless excluded either explicitly or clearly from the context of the embodiment or aspect.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

BRIEF DESCRIPTION OF THE DRAWINGS

The FIGURE depicts a graph representing cumulative mortality data over time for all houses in large-scale animal study.

DETAILED DESCRIPTION

A variety of microbial species have been shown to have certain degrees of efficacy against gut pathogens either in vitro or in vivo. As described in more detail herein, the inventors have surprisingly discovered that administering specific species of organic acid (such as, lactic acid)-producing microbes to animals (such as domesticated birds, for example, chickens) can improve performance on one or more metrics that include increased bodyweight gain, intestinal health status, decreased feed conversion ratio (FCR), improved gut barrier integrity, reduced mortality, reduced pathogen infection (such as, but not limited to, infection by

*Clostridium perfringens*), and reduced pathogen shedding in feces. Without being bound to theory, it is believed that metabolites of organic acid-producing bacteria play an important role in the prevention of intestinal inflammation and in the maintenance of intestinal homeostasis. While many bacterial species have the capability to produce organic acids, not all species can provide benefits to animals when administered as a feed additive or as part of a feed. However, as will be described in the Examples section, administration of particular combinations of microbials was discovered to be surprisingly effective in the prevention and/or treatment of gut pathogenesis in animals as well as for maintenance of overall health.

I. Definitions

"Organic acids," as used herein, refers to an organic compound with acidic properties. In some non-limiting embodiments, organic acid compounds are selected from the group consisting of lactic acid (2-hydroxypropionic acid), succinic acid, furandicarboxylic acid, fumaric acid, maleic acid, citric acid, glutamic acid, aspartic acid, acrylic acid, oxalic acid, and glucanic acid. Other non-limiting organic acids include formic acid (methanoic acid), acetic acid (ethanoic acid), propionic acid (propanoic acid), butanoic acid (butyric acid), isobutyric acid (2-methylpropanoic acid), valeric acid (pentanoic acid), and isovaleric acid (3-methylbutanoic acid). Inclusive in this definition of organic acids are also the conjugate bases of organic acids including, for example, lactate, glutamate, fumarate, malate, formate, acetate, propionate, butyrate, isobutyrate, valerate, isovalerate etc.

As used herein, "microorganism" or "microbe" refers to a bacterium, a fungus, a virus, a protozoan, and other microbes or microscopic organisms.

As used here in the term "direct fed microbial" refers to a composition for consumption by animals (i.e. as an or as a component of animal feed) that contains viable microorganisms, i.e. microorganisms that are capable of living and reproducing. See, for example, U.S. Pat. No. 8,420,074. A direct fed microbial may comprise one or more (such as any of 1, 2, 3, 4, 5, or 6 or more) of any of the microbial strains described herein.

A bacterial "strain" as used herein refers to a bacterium which remains genetically unchanged when grown or multiplied. The multiplicity of identical bacteria is included.

By "at least one strain," is meant a single strain but also mixtures of strains comprising at least two strains of microorganisms. By "a mixture of at least two strains," is meant a mixture of two, three, four, five, six or even more strains. In some embodiments of a mixture of strains, the proportions can vary from 1% to 99%. When a mixture comprises more than two strains, the strains can be present in substantially equal proportions in the mixture or in different proportions.

For purposes of this disclosure, a "biologically pure strain" means a strain containing no other bacterial strains in quantities sufficient to interfere with replication of the strain or to be detectable by normal bacteriological techniques. "Isolated," when used in connection with the organisms and cultures described herein, includes not only a biologically pure strain, but also any culture of organisms which is grown or maintained other than as it is found in nature. In some embodiments, the strains are mutants, variants, or derivatives of strains A1, A2, A3, D1, D2, D3, H1, H2, H3, S1, S2, and S3 that also provide benefits comparable to that provided by A1, A2, A3, D1, D2, D3, H1, H2, H3, S1, S2, and S3. In some embodiments, the strains are strains having all of the identifying characteristics of strains A1, A2, A3, D1, D2, D3, H1, H2, H3, S1, S2, and S3. Further, each individual strain (A1, A2, A3, D1, D2, D3, H1, H2, H3, S1, S2, and S3) or any combination of these strains can also provide one or more of the benefits described herein. It will also be clear that addition of other microbial strains, carriers, additives, enzymes, yeast, or the like will also provide one or more benefits or improvement of one or more metrics in an animal and will not constitute a substantially different DFM.

The term "16S rRNA" or "16S ribosomal RNA" means the rRNA constituting the small subunit of prokaryotic ribosomes. In bacteria, this sequence can be used to identify and characterize operational taxonomic units.

The term "sequence identity" or "sequence similarity" as used herein, means that two polynucleotide sequences, a candidate sequence and a reference sequence, are identical (i.e. 100% sequence identity) or similar (i.e. on a nucleotide-by-nucleotide basis) over the length of the candidate sequence. In comparing a candidate sequence to a reference sequence, the candidate sequence may comprise additions or deletions (i.e. gaps) as compared to the reference sequence (which does not comprise additions or deletions) for optimal alignment of the two sequences. Optimal alignment of sequences for determining sequence identity may be conducted using the any number of publicly available local alignment algorithms known in the art such as ALIGN or Megalign (DNASTAR), or by inspection.

The term "percent (%) sequence identity" or "percent (%) sequence similarity," as used herein with respect to a reference sequence is defined as the percentage of nucleotide residues in a candidate sequence that are identical to the residues in the reference polynucleotide sequence after optimal alignment of the sequences and introducing gaps, if necessary, to achieve the maximum percent sequence identity.

As used herein, "prevent," "preventing," "prevention" and grammatical variations thereof refers to a method of partially or completely delaying or precluding the onset or recurrence of a disorder or condition (such as necrotic enteritis) and/or one or more of its attendant symptoms or barring an animal from acquiring or reacquiring a disorder or condition or reducing an animal's risk of acquiring or reacquiring a disorder or condition or one or more of its attendant symptoms.

As used herein, the term "reducing" in relation to a particular trait, characteristic, feature, biological process, or phenomena refers to a decrease in the particular trait, characteristic, feature, biological process, or phenomena. The trait, characteristic, feature, biological process, or phenomena can be decreased by 5%, 10%, 15%, 20%, 25%, 30%, 35%, 40%, 45%, 50%, 55%, 60%, 65%, 70%, 75%, 80%, 85%, 90%, 95%, 100% or greater than 100%.

The term "poultry," as used herein, means domesticated birds kept by humans for their eggs, their meat or their feathers. These birds are most typically members of the superorder Galloanserae, especially the order Galliformes which includes, without limitation, chickens, quails, ducks, geese, emus, ostriches, pheasant, and turkeys.

As used herein "administer" or "administering" is meant the action of introducing one or more microbial strain, an exogenous feed enzyme and/or a strain and an exogenous feed enzyme to an animal, such as by feeding or by gavage.

As used herein, "effective amount" means a quantity of DFM and/or exogenous enzymes to improve one or more metrics in an animal. Improvement in one or more metrics of an animal (such as, without limitation, any of increased bodyweight gain, intestinal health status, decreased feed conversion ratio (FCR), improved gut barrier integrity, reduced mortality, reduced pathogen infection, and reduced pathogen shedding in feces) can be measured as described herein or by other methods known in the art. An effective amount can be administered to the animal by providing ad libitum access to feed containing the DFM and exogenous enzymes. The DFM and exogenous enzymes can also be administered in one or more doses.

The term "intestinal health status" refers to the status of the gut wall structure and morphology which can be affected by, for example, infectious agents or a non-infectious cause, such as a suboptimal formulated diet. "Gut wall structure and morphology" or "gut barrier integrity" can refer to, without limitation, epithelial damage and epithelial permeability which is characterized by a shortening of villi, a lengthening of crypts and an infiltration of inflammatory cells (such as, without limitation, CD3+ cells). The latter damage and inflammation markers can also be associated with a "severe" macroscopic appearance of the gut—compared to a "normal" appearance-when evaluated using a scoring system such as the one described by Teirlynck et al. (2011).

As used herein, the term "feed" is used synonymously herein with "feedstuff." Feed broadly refers to a material, liquid or solid, that is used for nourishing an animal, and for sustaining normal or accelerated growth of an animal including newborns or young and developing animals. The term includes a compound, preparation, mixture, or composition suitable for intake by an animal (such as, e.g., for poultry such as quail, ducks, turkeys, and chickens). In some embodiments, a feed or feed composition comprises a basal food composition and one or more feed additives or feed additive compositions. The term "feed additive" as used herein refers to components included for purposes of fortifying basic feed with additional components to promote feed intake, treat or prevent disease, or alter metabolism. Feed additives include pre-mixes. In other embodiments, a feed additive refers to a composition that supplements a feed but is not necessarily a component of the feed or food. For example, in one embodiment, the feed additive composition supplements a feed via delivery through a fluid (such as water) that is administered to the animal separately from the feed or food (for example, via a waterline or water distribution system).

A "premix," as referred to herein, may be a composition composed of micro-ingredients such as, but not limited to, one or more of vitamins, minerals, chemical preservatives, antibiotics, fermentation products, and other essential ingredients. Premixes are usually compositions suitable for blending into commercial rations.

As used herein, "improving one or more metrics in an animal" refers to improvements on measurements relevant to the growth and/or health of an animal (such as a domesticated bird, for example, a chicken), measured by one or more of the following parameters: average daily weight gain (ADG), overall weight, mortality, feed conversion (which includes both feed:gain and gain:feed), feed intake, intestinal health status, decreased feed conversion ratio (FCR), improved gut barrier integrity, reduced mortality, reduced pathogen infection, and reduced pathogen shedding in feces. "An improvement in a metric" or "improved metric" as used herein, refers to an improvement in at least one of the parameters listed under the metrics in an animal definition.

As used herein, the term "feed conversion ratio" (FCR) refers to the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

The phrase "antibiotic resistance genes" or "antimicrobial resistance (AMR) genes," as used interchangeably herein, refers to genes that confer resistance to antibiotics, for example by coding for enzymes which destroy it, by coding for surface proteins which prevent it from entering a microorganism, actively exports it, or by being a mutant form of the antibiotic's target so that it can ignore it. Examples of AMR genes may be found on the ARDB—Antibiotic Resistance Genes Database (Center for Bioinformatics and Computational Biology, University of Maryland, College Park, MD 20742; gene. Hypertext Transfer Protocol Secure:// ardb.cbcb.umd.edu/). Non-limiting examples of AMR genes include but are not limited to extended-spectrum beta lactamse (ESBL) genes, methicillin resistance gene, CTX-M-15; ndm-1,2,5,6, a vancomycin resistance, lnuC (a nucleotidyltransferase), vatE, (an acctyltransferase), or tetW. In some embodiments, one or more AMR genes can be associated with a mobile genetic element (such as a transposon) near the gene (such as within any of about 10 kb, 9 kb, 8 kb, 7 kb, 6 kb, 5 kb, 4 kb, 3 kb, 2 kb, 1 kb, 0.5 kb or closer to the gene, including distances falling in between any of these values). In other embodiments, one or more AMR genes are not associated with a mobile genetic element, such as a transposon.

As used herein "mobile genetic element' is meant to include any type of nucleic acid molecule that is capable of movement within a genome or from one genome to another. For example, these can include, without limitation, transposons or transposable elements (including retrotransposons, DNA transposons, and insertion sequences); plasmids; bacteriophage elements (including Mu; and group II introns).

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number. For example, in connection with a numerical value, the term "about" refers to a range of −10% to +10% of the numerical value, unless the term is otherwise specifically defined in context.

As used herein, the singular terms "a," "an," and "the" include the plural reference unless the context clearly indicates otherwise.

It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

It is also noted that the term "consisting essentially of," as used herein refers to a composition wherein the component(s) after the term is in the presence of other known component(s) in a total amount that is less than 30% by weight of the total composition and do not contribute to or interferes with the actions or activities of the component(s).

It is further noted that the term "comprising," as used herein, means including, but not limited to, the component(s) after the term "comprising." The component(s) after the term "comprising" are required or mandatory, but the composition comprising the component(s) can further include other non-mandatory or optional component(s).

It is also noted that the term "consisting of," as used herein, means including, and limited to, the component(s) after the term "consisting of." The component(s) after the term "consisting of" are therefore required or mandatory, and no other component(s) are present in the composition.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Unless defined otherwise herein, all technical and scientific terms used herein have the same meaning as commonly understood by one of ordinary skill in the art to which this invention pertains.

Other definitions of terms may appear throughout the specification.

II. Compositions

A. Strains

Direct fed microbials (DFMs) refer to the feeding of beneficial microbes to animals, such as domestic birds, when they are under periods of stress (disease, ration changes, environmental or production challenges) or as a part of a daily nutritional regimen to prevent disease and facilitate nutrient usage during digestion. Probiotics is another term for this category of feed additives. Probiotics or DFMs have been shown to improve animal performance in controlled studies. In some embodiments, DFMs include both direct fed bacteria and/or yeast-based products and, in particular embodiments, include viable microorganisms. The term "viable microorganism" means a microorganism which is metabolically active or able to differentiate.

In one embodiment, the DFM may be a spore forming bacterium and hence the term DFM may refer to a composition that is comprised of or contains spores, e.g., bacterial spores. Therefore, in one embodiment the term "viable microorganism" as used herein may include microbial spores, such as endospores or conidia. In another embodiment, the DFM in the feed additive composition according to the present invention is not comprised of or does not contain microbial spores, e.g. endospores or conidia (i.e., the DFM is non-spore forming).

The strains provided herein include *Lactobacillus reuteri* strain S1, *L. reuteri* strain S2, *L. reuteri* strain S3, *L. gallinarum* strain H1, *L. salivarius* strain H2, *L. agilis* strain H3, *L. salivarius* strain A1, *L. reuteri* strain A2, *L. reuteri* strain A3, *L. agilis* strain D1, *L. salivarius* strain D2, and *L. crispatus* strain D3, which are also referred to herein as S1, S2, S3, H1, H2, H3, A1, A2, A3, D1, D2, and D3, respectively.

*L. reuteri* strain S1, *L. reuteri* strain S2, *L. reuteri* strain S3, *L. reuteri* strain A2, *L. gallinarum* strain H1, *L. salivarius* strain H2, and *L. agilis* strain H3 were deposited on Jul. 24, 2019 at the Westerdijk Fungal Biodiversity Institute (WFDB), Uppsalalaan 8, 3584 CT, Utrecht, The Netherlands and given accession numbers CBS 145921, CBS 145922, CBS 145923, CBS 145924, CBS145918, CBS145919, and CBS 145920, respectively. The deposits were made under the provisions of the Budapest Treaty on the International Recognition of the Deposit of Microorganisms for the Purposes of Patent Procedure. One or more strain provided herein can be used as a direct-fed microbial (DFM).

The DFM strains disclosed herein are primarily found in the genus *Lactobacillus*. As of March 2020, Lactobacilli comprised 261 species that are extremely diverse at phenotypic, ecological and genotypic. Given recent advances in whole genome sequencing and comparative genomics, the genus *Lactobacillus* was recently divided into 25 separate genera with strains belonging to previously designated Lactobacilli species being transferred to new species and/or genera (see Zheng et al., 2020, *Int. J. Syst. Evol. Microbiol.*, 70:2782-2858; Pot et al., *Trends in Food Science & Technology* 94 (2019) 105-113; and Koutsoumanis et al., 2020, *EFSA Journal*, 18 (7): 6174 the disclosures of each of which are incorporated by reference herein). For purposes of the instant disclosure, the previous classification of *Lactobacillus* species will continue to be employed. However, in some embodiments *Lactobacillus agilis* is also classified as as Ligilactobacillus *agilis*. In other embodiments, *Lactobacillus salivarius* is also classified as Ligilactobacillus *salivarius*. In further embodiments, *Lactobacillus reuteri* is also classified as Limosilactobacillus *reuteri*.

DFM compositions can include those that contain one or more strains (such as any of about 1, 2, 3, 4, 5, 6, 7, or 8 or more strains) of *Lactobacillus reuteri*; and/or *L. salivarius*. *L. reuteri* is a gram-positive bacterium that naturally inhabits the gut of mammals and birds. First described in the early 1980s, some strains of *L. reuteri* are used as probiotics. Some *L. reuteri* can produce a novel broad-spectrum antibiotic substance known as reuterin. *Lactobacillus salivarius* is a probiotic bacteria species that has been found to live in the gastrointestinal tract and exert a range of therapeutic properties including suppression of pathogenic bacteria. The DFM composition can further include those that contain one or more strains (such as any of about 1, 2, 3, 4, 5, 6, 7, or 8 or more strains) of *L. agilis*, *L. crispatus*, and/or *L. gallinarum*.

The DFM composition can also include only strains of *L. reuteri* (such as 1, 2, 3, 4, 5, 6, 7, or 8 strains of *L. reuteri* without any other microbials present). For example, the DFM composition can include one or more of *L. reuteri* strains S1, S2, and/or S3 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *L. reuteri* strain S1 (SEQ ID NO: 7), S2 (SEQ ID NO: 8), and/or S3 (SEQ ID NO: 9). In some embodiments, the DFM composition includes only *L. reuteri* strain S1, S2, or S3. In another embodiment, DFM composition includes *L. reuteri* strains S1 and S2; *L. reuteri* strains S1 and S3; *L. reuteri* strains S2 and S3; or *L. reuteri* strains S1, S2, and S3. Additionally, when cultured together, one or more *L. reuteri* strains S1, S2, and/or S3 have one or more physiological or metabolic properties that individually cultured *L. reuteri* strains lack. These properties can include, without limitation, changes in the amount and/or type of organic acid produced, change in metabolic profile, and/or a change in the composition of media in which the bacteria are cultured together (such as lactate).

The DFM compositions provided herein can include one or more of *L. reuteri* strains S1, S2, and/or S3 (i.e. the compositions include the actual bacteria from these strains)

and/or one or more culture supernatants derived from the culturing of these strains (individually or in co-culture).

DFM compositions can additionally include those that contain one or more of *L. salivarius* microbes, *L. gallinarum* microbes, *L. agilis* microbes, and/or *L. reuteri* microbes.

The DFM composition can include one or more of *L. salivarius* strain H2, *L. gallinarum* strain H1, *L. reuteri* strain A2, and/or *L. agilis* strain H3 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *L. salivarius* strain H2 (SEQ ID NO: 10), *L. gallinarum* strain H1 (SEQ ID NO: 11), *L. reuteri* strain A2 (SEQ ID NO: 12), and/or *L. agilis* strain H3 (SEQ ID NO: 1). In some embodiments, the DFM composition includes only *L. salivarius* strain H2, *L. gallinarum* strain H1, *L. reuteri* strain A2, or *L. agilis* strain H3. In another embodiment, the DFM composition includes *L. salivarius* strain H2 and *L. gallinarum* strain H1; *L. salivarius* strain H2 and *L. reuteri* strain A2; *L. salivarius* strain H2 and *L. agilis* strain H3; *L. gallinarum* strain H1 and *L. reuteri* strain A2; *L. gallinarum* strain H1 and *L. agilis* strain H3; *L. reuteri* strain A2 and *L. agilis* strain H3; *L. salivarius* strain H2, *L. gallinarum* strain H1, and *L. reuteri* strain A2; *L. salivarius* strain H2, *L. reuteri* strain A2, and *L. agilis* strain H3; *L. gallinarum* strain H1, *L. reuteri* strain A2, and *L. agilis* strain H3; *L. salivarius* strain H2, *L. gallinarum* strain H1, *L. reuteri* strain A2, and *L. agilis* strain H3; *L. salivarius* strain H2, *L. gallinarum* strain H1, and *L. reuteri* strain A2; or *L. salivarius* strain H2, *L. gallinarum* strain H1, and *L. agilis* strain H3. Additionally, when cultured together, one or more *L. salivarius* strain H2, *L. gallinarum* strain H1, *L. reuteri* strain A2, and/or *L. agilis* strain H3 (such as *L. salivarius* strain H2, *L. gallinarum* strain H1, and *L. reuteri* strain A2; or *L. salivarius* strain H2, *L. gallinarum* strain H1, and *L. agilis* strain H3) have one or more physiological or metabolic properties that individually cultured strains lack. These properties can include, without limitation, changes in the amount and/or type of organic acid production (such as the production of lactic acid).

The DFM compositions provided herein can include one or more *L. salivarius* strain H2, *L. gallinarum* strain H1, *L. reuteri* strain A2, and/or *L. agilis* strain H3 (such as *L. salivarius* strain H2, *L. gallinarum* strain H1, and *L. reuteri* strain A2; or *L. salivarius* strain H2, *L. gallinarum* strain H1, and *L. agilis* strain H3) (i.e. the compositions include the actual bacteria from these strains) and/or one or more culture supernatants derived from the culturing of these strains (individually or in co-culture).

DFM compositions can additionally include those that contain one or more of *L. salivarius* microbes, *L. agilis* microbes, and/or *L. reuteri* microbes.

The DFM composition can include one or more of *L. salivarius* strain A1, *L. reuteri* strain A2, and/or *L. agilis* strain A3 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *L. salivarius* strain A1 (SEQ ID NO: 9), *L. reuteri* strain A2 (SEQ ID NO: 10), and/or *L. agilis* strain A3 (SEQ ID NO: 11). In some embodiments, the DFM composition includes only *L. salivarius* strain A1, *L. reuteri* strain A2, or *L. agilis* strain A3. In another embodiment, the DFM composition includes *L. salivarius* strain A1 and *L. reuteri* strain A2; *L. salivarius* strain A1 and *L. agilis* strain A3; *L. reuteri* strain A2 and *L.

*agilis* strain A3; *L. salivarius* strain A1, *L. reuteri* strain A2, and *L. agilis* strain A3. Additionally, when cultured together, one or more *L. salivarius* strain A1, *L. reuteri* strain A2, and/or *L. agilis* strain A3 have one or more physiological or metabolic properties that individually cultured strains lack. These properties can include, without limitation, changes in the amount and/or type of organic acid produced (such as the production of lactic acid) change in metabolic profile, and/or a change in the composition of media in which the bacteria are cultured together.

The DFM compositions provided herein can include one or more of *L. salivarius* strain A1, *L. reuteri* strain A2, and/or *L. agilis* strain A3 (i.e. the compositions include the actual bacteria from these strains) and/or one or more culture supernatants derived from the culturing of these strains (individually or in co-culture).

DFM compositions can additionally include those that contain one or more of *L. salivarius* microbes, *L. agilis* microbes, and/or *L. crispatus* microbes.

The DFM composition can include one or more of *L. agilis* strain D1, *L. salivarius* strain D2, and/or *L. crispatus* strain D3 or one or more microbe(s) having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of one or more of *L. agilis* strain D1 (SEQ ID NO: 5), *L. salivarius* strain D2 (SEQ ID NO: 4), and/or *L. crispatus* strain D3 (SEQ ID NO: 6). In some embodiments, the DFM composition includes only *L. agilis* strain D1, *L. salivarius* strain D2, or *L. crispatus* strain D3. In another embodiment, the DFM composition includes *L. agilis* strain D1 and *L. salivarius* strain D2; *L. agilis* strain D1 and *L. crispatus* strain D3; *L. salivarius* strain D2 and *L. crispatus* strain D3; *L. agilis* strain D1, *L. salivarius* strain D2, and *L. crispatus* strain D3. Additionally, when cultured together, one or more *L. agilis* strain D1, *L. salivarius* strain D2, and/or *L. crispatus* strain D3 have one or more physiological or metabolic properties that individually cultured strains lack. These properties can include, without limitation, changes in the amount and/or type of organic acid produced (such as the production of lactic acid) change in metabolic profile, and/or a change in the composition of media in which the bacteria are cultured together.

The DFM compositions provided herein can include one or more *L. agilis* strain D1, *L. salivarius* strain D2, and/or *L. crispatus* strain D3 (i.e. the compositions include the actual bacteria from these strains) and/or one or more culture supernatants derived from the culturing of these strains (individually or in co-culture).

In some embodiments, one or more of (such as any of 1, 2, 3, 4, 5, 6, 7, 8, 9, 10, or 11) the strains provided herein including *L. reuteri* strain S1 (CBS 145921), *L. reuteri* strain S2 (CBS 145922), *L. reuteri* strain S3 (CBS 145923), *L. gallinarum* strain H1 (CBS145918), *L. salivarius* strain H2 (CBS 145919), *L. reuteri* strain A2 (CBS 145924), *L. agilis* strain H3, *L. salivarius* strain A1, *L. agilis* strain A3, *L. agilis* strain D1, *L. salivarius* strain D2, and *L. crispatus* strain D3 further comprise one or more (such as any of 1, 2, 3, 4, 5, 6, 7, 8, 9, 10 or more) inactivated or deleted AMR genes.

B. Exogenous Enzymes

Supplemental enzymes can be used as additives to animal feed, particularly poultry and swine feeds, as a means to improve nutrient utilization and performance characteristics.

In one embodiment, the disclosure relates to a composition comprising one or more DFM (such as DFMs containing any of the microbial strains disclosed herein) and one or more exogenous feed enzymes. In another embodiment, the disclosure relates to a composition comprising, consisting of, or consisting essentially of a multi-strain DFM (such as any of the multi-strain DFM compositions disclosed herein) and one or more exogenous feed enzymes. In one embodiment, the exogenous feed enzymes include, but are not limited to, xylanase, amylase, phytase, beta-glucanase, and protease. In still another embodiment, the composition comprises a feed additive.

1. Xylanases

Xylanase is the name given to a class of enzymes that degrade the linear polysaccharide β-1,4-xylan into xylose, thus breaking down hemicellulose, one of the major components of plant cell walls. Xylanases, e.g., endo-β-xylanases (EC 3.2.1.8) hydrolyze the xylan backbone chain. In one embodiment, provided herein are compositions comprising a multi-strain DFM (such as any of the multi-strain DFM compositions disclosed herein) and one or more xylanase.

In one embodiment, the xylanase may be any commercially available xylanase. Suitably the xylanase may be an endo-1,4-P-d-xylanase (classified as E.G. 3.2.1.8) or a 1,4β-xylosidase (classified as E.G. 3.2.1.37). In one embodiment, the disclosure relates to a DFM in combination with an endoxylanase, e.g. an endo-1,4-P-d-xylanase, and another enzyme. All E.C. enzyme classifications referred to herein relate to the classifications provided in Enzyme Nomenclature—Recommendations (1992) of the nomenclature committee of the International Union of Biochemistry and Molecular Biology—ISBN 0-12-226164-3, which is incorporated herein In another embodiment, the xylanase may be a xylanase from *Bacillus*, Trichodermna, Therinomyces, *Aspergillus* and *Penicillium*. In still another embodiment, the xylanase may be the xylanase in Axtra XAP® or Avizyme 1502®, both commercially available products from Danisco A/S. In one embodiment, the xylanase may be a mixture of two or more xylanases. In still another embodiment, the xylanase is an endo-1,4-β-xylanase or a 1,4-β-xylosidase. In yet another embodiment, the xylanase is from an organism selected from the group consisting of: *Bacillus, Trichoderma, Thermomyces, Aspergillus, Penicillium*, and *Humicola*.

In one embodiment, the disclosure relates to a composition comprising a multi-strain DFM (such as any of the multi-strain DFM compositions disclosed herein) and xylanase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 xylanase units/g of composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, and greater than 8000 xylanase units/g composition.

It will be understood that one xylanase unit (XU) is the amount of enzyme that releases 0.5 μmol of reducing sugar equivalents (as xylose by the Dinitrosalicylic acid (DNS) assay-reducing sugar method) from an oat-spelt-xylan substrate per min at pH 5.3 and 50° C. (Bailey, et al., *Journal of Biotechnology*, Volume 23, (3), May 1992, 257-270).

2. Amylases

Amylase is a class of enzymes capable of hydrolysing starch to shorter-chain oligosaccharides, such as maltose. The glucose moiety can then be more easily transferred from maltose to a monoglyceride or glycosylmonoglyceride than from the original starch molecule. The term amylase includes α-amylases (E.G. 3.2.1.1), G4-forming amylases (E.G. 3.2.1.60), β-amylases (E.G. 3.2.1.2) and γ-amylases (E.C. 3.2.1.3). Amylases may be of bacterial or fungal origin, or chemically modified or protein engineered mutants. In one embodiment, provided herein are compositions comprising a multi-strain DFM (such as any of the multi-strain DFM compositions disclosed herein) and one or more amylase.

In one embodiment, the amylase may be a mixture of two or more amylases. In another embodiment, the amylase may be an amylase, e.g. an α-amylase, from *Bacillus lichenifor-mis* and an amylase, e.g. an α-amylase, from *Bacillus amyloliquefaciens*. In one embodiment, the α-amylase may be the α-amylase in Axtra XAP® or Avizyme 1502®, both commercially available products from Danisco A/S. In yet another embodiment, the amylase may be a pepsin resistant α-amylase, such as a pepsin resistant *Trichoderma* (such as *Trichoderma reesei*) alpha amylase. A suitably pepsin resistant α-amylase is taught in UK application number 101 1513.7 (which is incorporated herein by reference) and PCT/IB2011/053018 (which is incorporated herein by reference).

It will be understood that one amylase unit (AU) is the amount of enzyme that releases 1 mmol of glucosidic linkages from a water insoluble cross-linked starch polymer substrate per min at pH 6.5 and 37° C. (this may be referred to herein as the assay for determining 1 AU).

In one embodiment, disclosure relates to a composition comprising a multi-strain DFM (such as any of the multi-strain DFM compositions disclosed herein) and amylase. In one embodiment, disclosure relates to a composition comprising a multi-strain DFM, xylanase and amylase. In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 amylase units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 amylase units/g composition.

3. Proteases

The term protease as used herein is synonymous with peptidase or proteinase. The protease may be a subtilisin (E.G. 3.4.21.62) or a bacillolysin (E.G. 3.4.24.28) or an alkaline serine protease (E.G. 3.4.21.x) or a keratinase (E.G. 3.4.X.X). In one embodiment, the protease is a subtilisin. Suitable proteases include those of animal, vegetable or microbial origin. Chemically modified or protein engineered mutants are also suitable. The protease may be a serine protease or a metalloprotease. e.g., an alkaline microbial protease or a trypsin-like protease. In one embodiment, provided herein are compositions comprising a multi-strain DFM (such as any of the multi-strain DFM compositions disclosed herein) and one or more protease.

Examples of alkaline proteases are subtilisins, especially those derived from *Bacillus* sp., e.g., subtilisin Novo, sub-tilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115.

In one embodiment, the protease is selected from the group consisting of subtilisin, a bacillolysin, an alkine serine protease, a keratinase, and a Nocardiopsis protease.

It will be understood that one protease unit (PU) is the amount of enzyme that liberates from the substrate (0.6% casein solution) one microgram of phenolic compound (expressed as tyrosine equivalents) in one minute at pH 7.5 (40 mM $Na_2PO_4$/lactic acid buffer) and 40° C. This may be referred to as the assay for determining 1 PU.

In one embodiment, disclosure relates to a composition comprising a multi-strain DFM (such as any of the multi-strain DFM compositions disclosed herein) and a protease. In another embodiment, disclosure relates to a composition comprising a multi-strain DFM (such as any of the multi-strain DFM compositions disclosed herein) and a xylanase and a protease. In still another embodiment, the disclosure relates to a composition comprising a multi-strain DFM (such as any of the multi-strain DFM compositions disclosed herein) and an amylase and a protease. In yet another embodiment, the disclosure relates to a composition comprising a multi-strain DFM (such as any of the multi-strain DFM compositions disclosed herein) and a xylanase, an amylase and a protease.

In one embodiment, the composition comprises 10-50, 50-100, 100-150, 150-200, 200-250, 250-300, 300-350, 350-400, 400-450, 450-500, 500-550, 550-600, 600-650, 650-700, 700-750, and greater than 750 protease units/g composition.

In one embodiment, the composition comprises 500-1000, 1000-1500, 1500-2000, 2000-2500, 2500-3000, 3000-3500, 3500-4000, 4000-4500, 4500-5000, 5000-5500, 5500-6000, 6000-6500, 6500-7000, 7000-7500, 7500-8000, 8000-8500, 8500-9000, 9000-9500, 9500-10000, 10000-11000, 11000-12000, 12000-13000, 13000-14000, 14000-15000 and greater than 15000 protease units/g composition.

4. Phytases

In one embodiment, provided herein are compositions comprising a multi-strain DFM (such as any of the multi-strain DFM compositions disclosed herein) and one or more phytase. The phytase for use in the present invention may be classified a 6-phytase (classified as E.C. 3.1.3.26) or a 3-phytase (classified as E.C. 3.1.3.8).

In one embodiment the phytase is a *Citrobacter* phytase derived from e.g. *Citrobacter freundii*, preferably *C. freundii* NCIMB 41247 and variants thereof e.g. as disclosed in WO2006/038062 (incorporated herein by reference) and WO2006/038128 (incorporated herein by reference), *Citrobacter braakii* YH-15 as disclosed in WO 2004/085638, *Citrobacter braakii* ATCC 51113 as disclosed in WO2006/037328 (incorporated herein by reference), as well as variants thereof e.g. as disclosed in WO2007/112739 (incorporated herein by reference) and WO2011/117396 (incorporated herein by reference), *Citrobacter amalonaticus*, preferably *Citrobacter amalonaticus* ATCC 25405 or *Citrobacter amalonaticus* ATCC 25407 as disclosed in WO2006037327 (incorporated herein by reference), *Citrobacter gillenii*, preferably *Citrobacter gillenii* DSM 13694 as disclosed in WO2006037327 (incorporated herein by reference), or *Citrobacter intermedius, Citrobacter koseri, Citrobacter murliniae, Citrobacter rodentium, Citrobacter sedlakii, Citrobacter werkmanii, Citrobacter youngae, Citrobacter* species polypeptides or variants thereof.

In some embodiments, the phytase is an *E. coli* phytase marketed under the name Phyzyme XP™ Danisco A/S. Alternatively, the phytase may be a *Buttiauxella* phytase, e.g. a *Buttiauxella agrestis* phytase, for example, the phytase enzymes taught in WO 2006/043178, WO 2008/097619, WO2009/129489, WO2008/092901, PCT/US2009/41011 or PCT/IB2010/051804, all of which are incorporated herein by reference.

In one embodiment, the phytase may be a phytase from *Hafnia*, e.g. from *Hafnia alvei*, such as the phytase enzyme(s) taught in US2008263688, which reference is incorporated herein by reference. In one embodiment, the phytase may be a phytase from *Aspergillus*, e.g. from *Apergillus orzyae*. In one embodiment, the phytase may be a phytase from *Penicillium*, e.g. from *Penicillium funiculo-sum*.

Preferably, the phytase is present in the feedstuff in range of about 200 FTU/kg to about 1000 FTU/kg feed, more preferably about 300 FTU/kg feed to about 750 FTU/kg feed, more preferably about 400 FTU/kg feed to about 500 FTU/kg feed. In one embodiment, the phytase is present in the feedstuff at more than about 200 FTU/kg feed, suitably more than about 300 FTU/kg feed, suitably more than about 400 FTU/kg feed. In one embodiment, the phytase is present in the feedstuff at less than about 1000 FTU/kg feed, suitably less than about 750 FTU/kg feed. Preferably, the phytase is present in the feed additive composition in range of about 40 FTU/g to about 40,000 FTU/g composition, more preferably about 80 FTU/g composition to about 20,000 FTU/g composition, and even more preferably about 100 FTU/g composition to about 10,000 FTU/g composition, and even more preferably about 200 FTU/g composition to about 10,000 FTU/g composition. In one embodiment, the phytase is present in the feed additive composition at more than about 40 FTU/g composition, suitably more than about 60 FTU/g composition, suitably more than about 100 FTU/g composition, suitably more than about 150 FTU/g composition, suitably more than about 200 FTU/g composition. In one embodiment, the phytase is present in the feed additive composition at less than about 40,000 FTU/g composition, suitably less than about 20,000 FTU/g composition, suitably less than about 15,000 FTU/g composition, suitably less than about 10,000 FTU/g composition.

It will be understood that as used herein 1 FTU (phytase unit) is defined as the amount of enzyme required to release 1 μmol of inorganic orthophosphate from a substrate in one minute under the reaction conditions defined in the ISO 2009 phytase assay—A standard assay for determining phytase activity and 1 FTU can be found at International Standard ISO/DIS 30024: 1-17, 2009. In one embodiment, the enzyme is classified using the E.C. classification above, and the E.C. classification designates an enzyme having that activity when tested in the assay taught herein for determining 1 FTU.

C. DFM Formulations

In one embodiment, the DFM (such as any of the multi-strain DFM compositions disclosed herein) and, optionally, exogenous enzymes may be formulated as a liquid, a dry powder or a granule. In one embodiment, the DFMs and exogenous enzymes can be formulated as a single mixture. In another embodiment, the DFMs and the exogenous enzymes can be formulated as separate mixtures. In still another embodiment, separate mixtures of DFMs and the exogenous enzymes can be administered at the same time or at different times. In still another embodiment, separate mixtures of DFMs and the exogenous enzymes can be administered simultaneously or sequentially. In yet another embodiment, a first mixture comprising DFMs can be administered followed by a second mixture comprising exogenous enzymes. In still another embodiment, a first mixture comprising exogenous enzymes can be administered followed by a second mixture comprising DFMs.

The dry powder or granules may be prepared by means known to those skilled in the art, such as, in top-spray fluid bed coater, in a buttom spray Wurster or by drum granulation (e.g. High sheer granulation), extrusion, pan coating or in a microingredients mixer.

In another embodiment, the DFM and/or the enzyme(s) may be coated, for example encapsulated. Suitably the DFM and enzymes may be formulated within the same coating or encapsulated within the same capsule. Alternatively, one or more of the enzymes may be formulated within the same coating or encapsulated within the same capsule while the DFM can be formulated in a separate coating from the enzymes.

In some embodiments, such as where the DFM is capable of producing endospores, the DFM may be provided without any coating. In such circumstances, the DFM endospores may be simply admixed with one or more enzymes. In the latter case, the enzymes may be coated, e.g. encapsulated, for instance one or more or all of the enzymes may be coated, e.g. encapsulated. The enzymes may be encapsulated as mixtures (i.e. comprising one or more, two or more, three or more or all) of enzymes or they may be encapsulated separately, e.g. as single enzymes. In one preferred embodiment, all enzymes may be coated, e.g. encapsulated, together. In one embodiment, the coating protects the enzymes from heat and may be considered a thermoprotectant.

In another embodiment, the DFMs and exogenous feed enzymes may be mixed with feed or administered in the drinking water, such as via a waterline. In one embodiment, the dosage range for inclusion into water is about $1\times10^3$ CFU/animal/day to about $1\times10^{15}$ CFU/animal/day, for example, about $1\times10^3$ CFU/animal/day, $1\times10^4$ CFU/animal/day, $1\times10^5$ CFU/animal/day, $1\times10^6$ CFU/animal/day, $1\times10^7$ CFU/animal/day, $1\times10^8$ CFU/animal/day, $1\times10^9$ CFU/animal/day $1\times10^{10}$ CFU/animal/day, $1\times10^{11}$ CFU/animal/day, $1\times10^{12}$ CFU/animal/day, $1\times10^{13}$ CFU/animal/day, $1\times10^{14}$ CFU/animal/day, or $1\times10^{15}$ CFU/animal/day, inclusive of all dosages falling in between these values.

D. Feed Additive Compositions

In one embodiment, provided herein are feed additive compositions comprising one or more DFMs (such as any of the multi-strain DFMs disclosed herein) and, optionally, one or more exogenous feed enzymes. In one embodiment, the feed additive composition can be formulated in any suitable way to ensure that the formulation comprises viable DFMs and, optionally, active enzymes.

In one embodiment, the feed additive composition may be used in the form of solid or liquid preparations or alternatives thereof. Examples of solid preparations include powders, pastes, boluses, capsules, ovules, pills, pellets, tablets, dusts, and granules which may be wettable, spray-dried or freeze-dried. Examples of liquid preparations include, but are not limited to, aqueous, organic or aqueous-organic solutions, suspensions and emulsions.

In another embodiment, the feed additive composition can be used in a solid form. In one embodiment, the solid form is a pelleted form. In solid form, the feed additive composition may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

In one embodiment, the feed additive composition is formulated to a dry powder or granules as described in WO2007/044968 (referred to as TPT granules) or WO 1997/016076 or WO 1992/012645 (each of which is incorporated herein by reference).

In one embodiment, the feed additive composition may be formulated to a granule feed composition comprising: an active agent comprising one or more DFM (such as any of the multi-strain DFM compositions disclosed herein) and, optionally, one or more exogenous feed enzyme and at least one coating. In one embodiment, the active agent of the granule retains activity after processing. In one embodiment, the active agent of the granule retains an activity level after processing selected from the group consisting of: 50-60% activity, 60-70% activity, 70-80% activity, 80-85% activity, 85-90% activity, and 90-95% activity.

In another embodiment, the granule may contain one coating. The coating may comprise a moisture hydrating material that constitutes at least 55% w/w of the granule. In another embodiment, the granule may contain two coatings. The two coatings may be a moisture hydrating coating and a moisture barrier coating. In some embodiments, the moisture hydrating coating may be from 25% to 60% w/w of the granule and the moisture barrier coating may be from 2% to 15% w/w of the granule. The moisture hydrating coating may be selected from inorganic salts, sucrose, starch, and maltodextrin and the moisture barrier coating may be selected from polymers, gums, whey and starch.

In yet another embodiment, the granule may be produced using a feed pelleting process and the feed pretreatment process may be conducted between 70° C. and 95° C. for up to several minutes, such as between 85° C. and 95° C. In another embodiment, the granule may be produced using a steam-heated pelleting process that may be conducted between 85° C. and 95° C. for up to several minutes.

In one embodiment, the granule may have a moisture barrier coating selected from polymers and gums and the moisture hydrating material may be an inorganic salt. The moisture hydrating coating may be between 25% and 45% w/w of the granule and the moisture barrier coating may be between 2% and 20% w/w of the granule.

In one embodiment, the active agent retains activity after conditions selected from one or more of: (a) a feed pelleting process; (b) a steam-heated feed pretreatment process; (c) storage; (d) storage as an ingredient in an unpelleted mixture; and (e) storage as an ingredient in a feed base mix or a feed premix comprising at least one compound selected from trace minerals, organic acids, reducing sugars, vitamins, choline chloride, and compounds which result in an acidic or a basic feed base mix or feed premix.

In some embodiments, the DFM (e.g. DFM endospores, for example) may be diluted using a diluent, such as starch powder, lime stone or the like. In one embodiment, the DFM and the enzymes may be in a liquid formulation suitable for consumption preferably such liquid consumption contains one or more of the following: a buffer, salt, sorbitol and/or glycerol. In another embodiment, the feed additive composition may be formulated by applying, e.g. spraying, the enzyme(s) onto a carrier substrate, such as ground wheat for example.

In one embodiment, the feed additive composition may be formulated as a premix. By way of example only, the premix may comprise one or more feed components, such as one or more minerals and/or one or more vitamins.

In one embodiment, the DFM and exogenous feed enzymes may be formulated with at least one physiologically acceptable carrier selected from at least one of maltodextrin, limestone (calcium carbonate), cyclodextrin, wheat or a wheat component, sucrose, starch, Na2SO4, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In another embodiment, the feed additive composition can be delivered as an aqueous suspension and/or an elixir. The feed additive composition may be combined with various sweetening or flavoring agents, coloring matter or dyes, with emulsifying and/or suspending agents and with diluents such as water, propylene glycol and glycerin, and combinations thereof. The feed additive composition may also be delivered as an aqueous suspension through a waterline.

E. Feedstuffs

In another embodiment, provided herein are feed additive compositions containing any of the multi-strain DFM compositions disclosed herein that may be used as a feed or in the preparation of a feed. The feed may be in the form of a solution or as a solid depending on the use and/or the mode of application and/or the mode of administration. When used as a feed or in the preparation of a feed, such as functional feed, the feed additive composition may be used in conjunction with one or more of the following: a nutritionally acceptable carrier, a nutritionally acceptable diluent, a nutritionally acceptable excipient, a nutritionally acceptable adjuvant, a nutritionally active ingredient.

In one embodiment, the feed additive composition disclosed herein is admixed with a feed component to form a feedstuff. In one embodiment, the feed may be a fodder, or a premix thereof, a compound feed, or a premix thereof. In one embodiment, the feed additive composition disclosed herein may be admixed with a compound feed, a compound feed component or a premix of a compound feed or to a fodder, a fodder component, or a premix of a fodder.

In one embodiment, fodder may be obtained from one or more of the plants selected from: alfalfa (lucerne), barley, birdsfoot trefoil, brassicas, Chau moellier, kale, rapeseed (canola), rutabaga (swede), turnip, clover, alsike clover, red clover, subterranean clover, white clover, grass, false oat grass, fescue, Bermuda grass, brome, heath grass, meadow grasses (from naturally mixed grassland swards, orchard grass, rye grass, Timothy-grass, corn (maize), millet, oats, sorghum, soybeans, trees (pollard tree shoots for tree-hay), wheat, and legumes.

Compound feeds can be complete feeds that provide all the daily required nutrients, concentrates that provide a part of the ration (protein, energy) or supplements that only provide additional micronutrients, such as minerals and vitamins. The main ingredients used in compound feed are the feed grains, which include corn, soybeans, sorghum, oats, and barley.

A "premix," as referred to herein, may be a composition composed of micro-ingredients such as vitamins, minerals, chemical preservatives, antibiotics, fermentation products, and other essential ingredients. Premixes are usually compositions suitable for blending into commercial rations.

In one embodiment, a feedstuff as disclosed herein may comprise one or more feed materials selected from the group comprising cereals, such as small grains (e.g., wheat, barley, rye, oats and combinations thereof) and/or large grains such as maize or sorghum; by products from cereals, such as corn gluten meal, Distillers Dried Grain Solubles (DDGS), wheat bran, wheat middlings, wheat shorts, rice bran, rice hulls, oat hulls, palm kernel, and citrus pulp; protein obtained from sources such as soya, sunflower, peanut, lupin, peas, fava beans, cotton, canola, fish meal, dried plasma protein, meat and bone meal, potato protein, whey, copra, sesame; oils and fats obtained from vegetable and animal sources; and minerals and vitamins.

In yet another embodiment, a feedstuff may comprise at least one high fiber feed material and/or at least one by-product of the at least one high fiber feed material to provide a high fiber feedstuff. Examples of high fiber feed materials include: wheat, barley, rye, oats, by products from cereals, such as corn gluten meal, Distillers Dried Grain Solubles (DDGS), wheat bran, wheat middlings, wheat shorts, rice bran, rice hulls, oat hulls, palm kernel, and citrus pulp. Some protein sources may also be regarded as high fiber: protein obtained from sources such as sunflower, lupin, fava beans and cotton In still another embodiment, the feed may be one or more of the following: a compound feed and premix, including pellets, nuts or (cattle) cake; a crop or crop residue: corn, soybeans, sorghum, oats, barley, corn stover, copra, straw, chaff, sugar beet waste; fish meal; freshly cut grass and other forage plants; meat and bone meal; molasses; oil cake and press cake; oligosaccharides; conserved forage plants: hay and silage; seaweed; seeds and grains, either whole or prepared by crushing, milling etc.; sprouted grains and legumes; yeast extract.

In one embodiment, the feed additive composition of disclosed herein is admixed with the product (e.g. feedstuff). Alternatively, the feed additive composition may be included in the emulsion or raw ingredients of a feedstuff. In another embodiment, the feed additive composition is made available on or to the surface of a product to be affected/treated. In still another embodiment, the feed additive compositions disclosed herein may be applied, interspersed, coated and/or impregnated to a product (e.g. feedstuff or raw ingredients of a feedstuff) with a controlled amount of DFM and, optionally, enzymes.

In yet another embodiment, the DFM and optional enzymes may be used simultaneously (e.g. when they are in admixture together or even when they are delivered by different routes) or sequentially (e.g. they may be delivered by different routes).

In one embodiment, the DFM and optional enzymes are applied to the feedstuff simultaneously. In yet another embodiment, the DFM and optional enzymes are admixed prior to being delivered to a feedstuff or to a raw ingredient of a feedstuff.

In one embodiment, the DFMs in the feed additive compositions disclosed herein can be added in suitable concentrations including but not limited to concentrations in the final feed product that offer a daily dose of from about $2 \times 10^3$ CFU to about $2 \times 10^{11}$ CFU, from about $2 \times 10^6$ to about $1 \times 10^{10}$, and from about $3.75 \times 10^7$ CFU to about $1 \times 10^{10}$ CFU.

III. Methods

A. Methods for Improving Performance Metrics in an Animal

Further provided herein are methods for increasing performance metrics of an animal. In another embodiment, the disclosure relates to methods of increasing performance metrics of a bird. In still another embodiment, the disclosure relates to methods of increasing performance metrics of poultry, including but not limited to broilers, chickens and turkeys.

In yet another embodiment, the disclosure relates to a method comprising administering to an animal a composition comprising DFMs (such as any of the multi-strain DFMs disclosed herein) and, optionally, exogenous feed enzymes. In still another embodiment, the disclosure relates to a method comprising administering to an animal an effective amount of a composition comprising DFMs and optional exogenous feed enzymes to increase performance of the animal. This effective amount can be administered to the animal in one or more doses. In one embodiment, the animal is poultry. In still another embodiment, the animal is a broiler.

In another embodiment, the disclosure relates to a method comprising administering to an animal (such as a domesticated bird, for example, a chicken) an effective amount of a composition comprising DFMs (such as any of the multi-strain DFMs disclosed herein) and optionally exogenous feed enzymes to increase average daily feed intake. In some embodiments, the average daily feed intake increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase average daily weight gain. In some embodiments, the average daily weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase total weight gain. In some embodiments, total weight gain increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase feed conversion, which can be measured by either feed:gain or gain:feed. In some embodiments, feed conversion increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase feed efficiency. In some embodiments, feed efficiency increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease mortality. In some embodiments, mortality decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease feed conversion ratio (FCR). In some embodiments, FCR decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to increase gut barrier integrity. In some embodiments, gut barrier integrity increases by any of about 10%, 15%, 20%, 25%, 30%, 35%, 40%, 45%, 50%, 55%, 60%, 65%, 70%, 75%, 80%, 85%, 90%, 95%, 100%, 105%, or 110%, inclusive of all values falling in between these percentages, relative to animals who are not administered one or more of the multi-strain DFM compositions disclosed herein. "Gut barrier integrity" can refer to, without limitation, epithelial damage and epithelial permeability which is characterized by a shortening of villi, a lengthening of crypts and an infiltration of inflammatory cells (such as, without limitation, CD3+ cells). The latter damage and inflammation markers can also be associated with a "severe" macroscopic appearance of the gut-compared to a "normal" appearance-when evaluated using a scoring system such as the one described by Teirlynck et al. (2011). In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease or prevent pathogen infection (such as, without limitation, infection by *Clostridium perfringens, Campylobacter jejuni*, a Salmonela sp., and/or *Escherichia coli*). In some embodiments, pathogen infection decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff. In some embodiments, the composition is a feed additive composition. In other embodiments, the composition is a feed or feedstuff.

In another embodiment, the disclosure relates to a method comprising administering to an animal (such as a domesticated bird, for example, a chicken) an effective amount of a composition comprising DFMs (such as any of the multi-strain DFMs disclosed herein) and optional exogenous feed enzymes to decrease or prevent pathogen shedding in the feces (such as, without limitation, shedding of *Clostridium perfringens, Campylobacter jejuni*, a Salmonela sp., and/or *Escherichia coli*). In some embodiments, pathogen shedding in the feces decreases by any of about 10%, 15%, 20%, 25%, 30%, 35%, 40%, 45%, 50%, 55%, 60%, 65%, 70%, 75%, 80%, 85%, 90%, 95%, or 100%, inclusive of all values falling in between these percentages, relative to animals who are not administered one or more of the multi-strain DFM compositions disclosed herein. In some embodiments, the composition is a feed additive composition. In other embodiments, the composition is a feed or feedstuff.

In still another embodiment, the DFM composition (such as a feed or feed additive composition) administered to the animal (such as a domesticated bird, for example, a chicken) is a multi-strain DFM comprising one or more of *L. reuteri* strain S1 (CBS 145921), or a strain having all of the identifying characteristics of *L. reuteri* strain S1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S1 (SEQ ID NO: 7); *L. reuteri* strain S2 (CBS 145922), or a strain having all of the identifying characteristics of *L. reuteri* strain S2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S2 (SEQ ID NO: 8); and/or *L. reuteri* strain S3 (CBS 145923), or a strain having all of the identifying characteristics of *L. reuteri* strain S3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S3 (SEQ ID NO: 9). In another embodiment, the DFM composition includes *L. reuteri* strains S1 and S2; *L. reuteri* strains S1 and S3; *L. reuteri* strains S2 and S3; or *L. reuteri* strains S1, S2, and S3. In some embodiments, the one or more (such as 1, 2, or 3) *L. reuteri* strain(s) is (are) administered to an animal at a rate of at least $1 \times 10^4$ CFU/animal/day. For poultry, according to one non-limiting embodiment, the one or more *L. reuteri* strain(s) can be fed at about $1 \times 10^5$ CFU/g feed to about $1 \times 10^{10}$ CFU/g feed. In at least some embodiments, the one or more *L. reuteri* strains is (are) fed at about $1 \times 10^5$ CFU/bird/day or about $1 \times 10^8$ CFU/bird/day.

In still another embodiment, the DFM composition (such as a feed or feed additive composition) administered to the animal (such as a domesticated bird, for example, a chicken) is a multi-strain DFM comprising one or more of *L. galli-narum.* strain H1 (CBS 145918), or a strain having all of the identifying characteristics *L. gallinarum.* strain H1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. gallinarum.* strain H1 (SEQ ID NO: 11); *L. salivarius* strain H2 (CBS 145919), or a strain having all of the identifying characteristics of *L. salivarius* strain H2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain H2 (SEQ ID NO: 10); *L. agilis* strain H3, or a strain having all of the identifying characteristics of *L. agilis* strain H3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain H3 (SEQ ID NO: 1); and/or *L. reuteri* strain A2 (CBS 145924), or a strain having all of the identifying characteristics of *L. reuteri* strain A2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain A2 (SEQ ID NO: 12). In some embodiments, the DFM composition includes only *L. gallinarum.* strain H1, *L. salivarius* strain H2, *L. agilis* strain H3, or *L. reuteri* strain A2. In another embodiment, the DFM composition includes *L. gallinarum.* strain H1 and *L. salivarius* strain H2; *L. reuteri* strain A2 and *L. agilis* strain H3; *L. gallinarum.* strain H1 and *L. reuteri* strain A2; *L. salivarius* strain H2 and *L. agilis* strain H3; *L. salivarius* strain H2 and *L. reuteri* strain A2; *L. agilis* strain H3 and *L. reuteri* strain A2; *L. gallinarum.* strain H1, *L. salivarius* strain H2, and *L. agilis* strain H3; *L. gallinarum.* strain H1, *L. agilis* strain H3, and *L. reuteri* strain A2; *L. salivarius* strain H2, *L. agilis* strain H3, and *L. reuteri* strain A2; *L. gallinarum.* strain H1, *L. salivarius* strain H2, and *L. agilis* strain H3; or *L. gallinarum.* strain H1, *L. salivarius* strain H2, and *L. reuteri* strain A2. In some embodiments, *L.*

*reuteri* strain A2 produces reuterin (3-hydroxypropionalde-hyde). In other embodiments, *L. reuteri* strain A2 does not produce reuterin (3-hydroxypropionaldehyde). In some embodiments, the one or more H1, H2, H3, and/or A2 strain(s) (such as H1, H2, and H3; or H1, H2, and A2) is (are) administered to an animal at a rate of at least $1 \times 10^4$ CFU/animal/day. For poultry, according to one non-limiting embodiment, the one or more H1, H2, H3, and/or A2 strain(s) (such as H1, H2, and H3; or H1, H2, and A2) can be fed at about $1 \times 10^5$ CFU/g feed to about $1 \times 10^{10}$ CFU/g feed. In at least some embodiments, the one or more H1, H2, H3, and/or A2 strain(s) (such as H1, H2, and H3; or H1, H2, and A2) strains is (are) fed at about $1 \times 10^5$ CFU/bird/day or about $1 \times 10^8$ CFU/bird/day.

In still another embodiment, the DFM composition (such as a feed or feed additive composition) administered to the animal (such as a domesticated bird, for example, a chicken) is a multi-strain DFM comprising one or more of *L. sali-varius* strain A1, or a strain having all of the identifying characteristics *L. salivarius* strain A1, or a microbe having a 16S ribosomal RNA sequence displaying at least about 97.0% sequence similarity (such as any of about 97%, 97.5%, 98%, 98.5%, 99%, 99.5%, or 100% sequence simi-larity) to a 16S ribosomal RNA sequence of *L. salivarius* strain A1 (SEQ ID NO: 2); *L. reuteri* strain A2 (CBS 145924), or a strain having all of the identifying character-istics of *L. reuteri* strain A2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain A2 (SEQ ID NO: 12); and/or *L. agilis* strain A3, or a strain having all of the identifying characteristics of *L. agilis* strain A3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain A3 (SEQ ID NO: 3). In some embodiments, *L. reuteri* strain A2 produces reuterin (3-hydroxypropionalde-hyde). In other embodiments, *L. reuteri* strain A2 does not produce reuterin (3-hydroxypropionaldehyde). In some embodiments, the DFM composition includes only *L. sali-varius* strain A1, *L. reuteri* strain A2, or *L. agilis* strain A3. In another embodiment, the DFM composition includes *L. salivarius* strain A1 and *L. reuteri* strain A2; *L. salivarius* strain A1 and *L. agilis* strain A3; *L. reuteri* strain A2 and *L. agilis* strain A3; or *L. salivarius* strain A1, *L. reuteri* strain A2, and *L. agilis* strain A3. In some embodiments, the one or more A1, A2 and/or A3 strain(s) is (are) administered to an animal at a rate of at least $1 \times 10^4$ CFU/animal/day. For poultry, according to one non-limiting embodiment, the one or more A1, A2 and/or A3 strain(s) can be fed at about $1 \times 10^5$ CFU/g feed to about $1 \times 10^{10}$ CFU/g feed. In at least some embodiments, the one or more A1, A2 and/or A3 strains is (are) fed at about $1 \times 10^5$ CFU/bird/day or about $1 \times 10^8$ CFU/bird/day.

In still another embodiment, the DFM composition (such as a feed or feed additive composition) administered to the animal (such as a domesticated bird, for example, a chicken) is a multi-strain DFM comprising one or more of *L. agilis* strain D1, or a strain having all of the identifying charac-teristics *L. agilis* strain D1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain D1 (SEQ ID NO: 5); *L. salivarius* strain D2, or a strain having all of the identifying characteristics of *L. salivarius* strain D2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain D2 (SEQ ID NO: 4); and/or *L. crispatus* strain D3, or a strain having all of the identifying characteristics of *L. crispatus* strain D3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. crispatus* strain D3 (SEQ ID NO: 6). In some embodiments, the DFM composition includes only *L. agilis* strain D1, *L. salivarius* strain D2, or *L. crispatus* strain D3. In another embodiment, the DFM composition includes *L. agilis* strain D1 and *L. salivarius* strain D2; *L. agilis* strain D1 and *L. crispatus* strain D3; *L. salivarius* strain D2 and *L. crispatus* strain D3; or *L. agilis* strain D1, *L. salivarius* strain D2, and *L. agilis* strain A3. In some embodiments, the one or more D1, D2 and/or D3 strain(s) is (are) administered to an animal at a rate of at least $1 \times 10^4$ CFU/animal/day. For poultry, according to one non-limiting embodiment, the one or more D1, D2 and/or D3 strain(s) can be fed at about $1 \times 10^5$ CFU/g feed to about $1 \times 10^{10}$ CFU/g feed. In at least some embodiments, the one or more D1, D2 and/or D3 strains is (are) fed at about $1 \times 10^5$ CFU/bird/day or about $1 \times 10^8$ CFU/bird/day.

The DFM compositions provided herein can be administered, for example, as a strain-containing culture solution, a strain-containing supernatant, or a bacterial product of a culture solution. Administration of a composition comprising a DFM and optional exogenous feed enzymes provided herein to an animal can increase the performance of the animal. In one embodiment, administration of a DFM provided herein to an animal can increase the average daily feed intake (ADFI), average daily gain (ADG), or feed efficiency (gain:feed; G:F) (collectively, "performance metrics"). One or more than one of these performance metrics may be improved.

The composition comprising DFMs and exogenous feed enzymes may be administered to the animal in one of many ways. For example, the composition can be administered in a solid form as a veterinary pharmaceutical, may be distributed in an excipient, preferably water (such as through a waterline), and directly fed to the animal, may be physically mixed with feed material in a dry form, or the composition may be formed into a solution and thereafter sprayed onto feed material. The method of administration of the compositions disclosed herein to the animal is considered to be within the skill of the artisan.

When used in combination with a feed material, the feed material can include corn, soybean meal, byproducts like distillers dried grains with solubles (DDGS), and vitamin/mineral supplement. Other feed materials can also be used.

Thus, in at least some embodiments, the effective amount of the composition comprising DFMs and optional exogenous feed enzymes is administered to an animal by supplementing a feed intended for the animal. As used herein, "supplementing," refers to the action of incorporating the effective amount of bacteria provided herein directly into the feed intended for the animal. Thus, the animal, when feeding, ingests the bacteria provided herein.

B. Methods for Preparing a Feed Additive Composition

Also provided herein are methods for preparing a feed additive composition comprising combining two or more of the DFMs disclosed herein. In some embodiments, the method includes combining two or more (such as any of 2 or 3) of *L. reuteri* strain S1 (CBS 145921), or a strain having all of the identifying characteristics of *L. reuteri* strain S1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S1 (SEQ ID NO: 7); *L. reuteri* strain S2 (CBS 145922), or a strain having all of the identifying characteristics of *L. reuteri* strain S2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S2 (SEQ ID NO: 8); *L. reuteri* strain S3 (CBS 145923), or a strain having all of the identifying characteristics of *L. reuteri* strain S3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain S3 (SEQ ID NO: 9). In another embodiment, *L. reuteri* strains S1 and S2 are combined; *L. reuteri* strains S1 and S3 are combined; *L. reuteri* strains S2 and S3 are combined; or *A. colihominis* strains S1, S2, and S3 are combined.

In yet further embodiments, the method includes combining two or more (such as any of 2, 3, or 4) of *L. gallinarum* strain H1 (CBS 145918), or a strain having all of the identifying characteristics *L. gallinarum* strain H1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. gallinarum* strain H1 (SEQ ID NO: 11); *L. salivarius* strain H2 (CBS 145919), or a strain having all of the identifying characteristics of *L. salivarius* strain H2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain H2 (SEQ ID NO: 10); *L. agilis* strain H3, or a strain having all of the identifying characteristics of *L. agilis* strain H3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain H3 (SEQ ID NO: 1); and/or *L. reuteri* strain A2 (CBS 145924), or a strain having all of the identifying characteristics of *L. reuteri* strain A2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain A2 (SEQ ID NO: 12). In another embodiment, *L. gallinarum* strain H1 and *L. salivarius* strain H2 are combined; *L. gallinarum* strain H1 and *L. agilis* strain H3 are combined; *L. gallinarum* strain H1 and *L. reuteri* strain A2 are combined; *L. salivarius* strain H2 and *L. agilis* strain H3 are combined; *L. salivarius* strain H2 and *L. reuteri* strain A2 are combined; *L. agilis* strain H3 and *L. reuteri* strain A2 are combined; *L. gallinarum* strain H1, *L. salivarius* strain H2, and *L. agilis* strain H3 are combined; *L. gallinarum* strain H1, *L. agilis* strain H3, and *L. reuteri* strain A2 are combined; *L. salivarius* strain H2, *L. agilis* strain H3, and *L. reuteri* strain A2 are combined; *L. gallinarum* strain H1, *L. salivarius* strain H2, *L. agilis* strain H3, and *L. reuteri* strain A2 are combined; *L. gallinarum* strain H1, *L. salivarius* strain H2, and *L. agilis* strain H3 are combined; or *L. gallinarum* strain H1, *L. salivarius* strain H2, and *L. reuteri* strain A2 are combined.

In additional embodiments, the method includes combining two or more (such as any of 2 or 3) of *L. salivarius* strain A1, or a strain having all of the identifying characteristics *L. salivarius* strain A1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain A1 (SEQ ID NO: 2); *L. reuteri* strain A2 (CBS 145924), or a strain having all of the identifying characteristics of *L. reuteri* strain A2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. reuteri* strain A2 (SEQ ID NO: 12); and/or *L. agilis* strain A3, or a strain having all of the identifying characteristics of *L. agilis* strain A3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain A3 (SEQ ID NO: 3). In another embodiment, *L. salivarius* strain A1 and *L. reuteri* strain A2 are combined; *L. salivarius* strain A1 and *L. agilis* strain A3 are combined; *L. reuteri* strain A2 and *L. agilis* strain A3 are combined; or *L. salivarius* strain A1, *L. reuteri* strain A2, and *L. agilis* strain A3 are combined.

In further embodiments, the method includes combining two or more (such as any of 2 or 3) of *L. agilis* strain D1, or a strain having all of the identifying characteristics *L. agilis* strain D1, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. agilis* strain D1 (SEQ ID NO: 5); *L. salivarius* strain D2, or a strain having all of the identifying characteristics of *L. salivarius* strain D2, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. salivarius* strain D2 (SEQ ID NO: 4); and/or *L. crispatus* strain D3, or a strain having all of the identifying characteristics of *L. crispatus* strain D3, or a microbe having a 16S ribosomal RNA sequence displaying at least about 97.0% sequence similarity (such as any of about 97%, 97.5%, 98%, 98.5%, 99%, 99.5%, or 100% sequence similarity) to a 16S ribosomal RNA sequence of *L. crispatus* strain D3 (SEQ ID NO: 6). In another embodiment, *L. agilis* strain D1 and *L. salivarius* strain D2 are combined; *L. agilis* strain D1 and *L. crispatus* strain D3 are combined; *L. salivarius* strain D2 and *L. crispatus* strain D3 are combined; or *L. agilis* strain D1, *L. salivarius* strain D2, and *L. crispatus* strain D3 are combined.

Additionally, the methods for preparing a feed additive composition can further include combining the feed additive composition with one or more of the exogenous enzymes disclosed herein (for example, one or more of a phytase, a protease, an amylase, a xylanase or a beta-glucanase). The method can additionally include a further step of packaging the feed additive composition for storage or transport.

C. Methods for Removing Antimicrobial Resistance (AMR) Genes

Bacteria have evolved to overcome a wide range of antibiotics, and resistance mechanisms against most of the conventional antibiotics have been identified in some bacteria. Accelerated development of newer antibiotics is being overrun by the pace of bacterial resistance. In the USA, for example, over 70% of hospital-acquired infections involve bacteria resistant to at least one antibiotic, and in Japan over 50% of the clinical isolates of *Staphylococcus aureus* are multidrug-resistant. Thus, removal of antimicrobial resistance (AMR) genes from probiotics/DFMs used for the prevention of intestinal inflammation and in the maintenance of intestinal homeostasis can in some instances be desirable.

AMR genes carried by a variety of bacteria are known in the art and the sequences of antibiotic resistance genes in any particular bacteria can be determined if desired. In certain non-limiting embodiments, the present disclosure includes CRISPR systems which comprise spacers encoding targeting RNA that is directed to bacterial DNA sequences which comprise antibiotic resistance genes. In some embodiments, the resistance gene confers resistance to a narrow-spectrum beta-lactam antibiotic of the penicillin class of antibiotics. In other embodiments, the resistance gene confers resistance to methicillin (e.g., methicillin or oxacillin), or flucloxacillin, or dicloxacillin, or some or all of these antibiotics.

Examples of AMR genes include, but are not limited to, fosfomycin resistance gene fosB, tetracycline resistance gene tetM, kanamycin nucleotidyltransferase aadD, bifunctional aminoglycoside modifying enzyme genes aacA-aphD, chloramphenicol acetyltransferase cat, mupirocin-resistance gene ileS2, vancomycin resistance genes vanX, vanR, vanH, vraE, vraD, methicillin resistance factor femA, fmtA, mecI, streptomycin adenylyltransferase spc1, spc2, antI, ant2, pectinomycin adenyltransferase spd, ant9, aadA2, lnuC, vatE, tetW, and any other resistance gene. In some embodiments, the AMRs are associated with one or more mobile genetic elements (such as a transposon) than can be located near the AMR gene (such as within any of about 10 kb, 9 kb, 8 kb, 7 kb, 6 kb, 5 kb, 4 kb, 3 kb, 2 kb, 1 kb, 0.5 kb or closer to the AMR gene, including distances falling in between any of these values).

AMRs can be identified or assayed qualitatively and/or quantitatively by any number of methods known in the art. For example, DNA can be extracted from microbial samples and assessed for the presence of antibiotic resistance genes using, e.g., quantitative PCR (qPCR), including multiplex quantitative PCR (qPCR). The microbial DNA array assay may test for a plurality of antibiotic resistance genes and facilitate testing for highly prevalent bacterial antibiotic resistance genes in a single reaction with both resistance gene identification (present vs absent) and quantitative profiling (expression relative to an internal standard). Other methods for identifying AMRs include, without limitation, whole genome sequencing via use of short-read sequencing technology (Illumina) and/or long-read sequencing technology platforms such as Oxford Nanopore Technology or PacBio or via the techniques used and discussed in Example 5. Once identified, AMR genes can be removed or inactivated using any number of standard molecular tools available in the art such as recombineering (Zhang et al., 2018, *J Bacteriol* 200; Ozcam et al., 2019, *Appl Environ Microbiol* 85, the disclosures of which are incorporated by reference herein), or CRISPR based methods (Oh & Van Pijkeren, 2014, *Nucleic Acids Res* 42:e131; U.S. Patent Application Publication No. 2017/0260546, the disclosures of which are incorporated by reference herein).

In some embodiments, one or more of (such as any of 1, 2, 3, 4, 5, 6, 7, 8, 9, 10, or 11) the strains provided herein including *L. reuteri* strain S1 (CBS 145921), *L. reuteri* strain S2 (CBS 145922), *L. reuteri* strain S3 (CBS 145923), *L. gallinarum* strain H1 (CBS145918), *L. salivarius* strain H2 (CBS 145919), *L. reuteri* strain A2 (CBS 145924), *L. agilis* strain H3, *L. salivarius* strain A1, *L. agilis* strain A3, *L. agilis* strain D1, *L. salivarius* strain D2, and *L. crispatus* strain D3 further comprise one or more (such as any of 1, 2, 3, 4, 5, 6, 7, 8, 9, 10 or more) inactivated or deleted AMR genes.

IV. Kits

Further provided herein are kits containing one or more of the DFMs (such as one or more of the multi-strain DFMs) disclosed herein. The kits can include one or more of (such as any of 1, 2, 3, 4, 5, 6, 7, 8, 9, 10, or 11) the strains provided herein including *L. reuteri* strain S1 (CBS 145921), *L. reuteri* strain S2 (CBS 145922), *L. reuteri* strain S3 (CBS 145923), *L. gallinarum* strain H1 (CBS145918), *L. salivarius* strain H2 (CBS 145919), *L. reuteri* strain A2 (CBS 145924), *L. agilis* strain H3, *L. salivarius* strain A1, *L. agilis* strain A3, *L. agilis* strain D1, *L. salivarius* strain D2, and *L. crispatus* strain D3 along with instructions for proper storage, maintenance, and use for administering to an animal to improve one or more performance metrics. In one embodiment, the kit can include strains S1, S2, and/or S3. In another embodiment, the kit can include strains H1, H2, H3, and/or A2 (such as H1, H2, and H3; or H1, H2, and A2). In a further embodiment, the kit can include strains A1, A2, and/or A3. In yet a further embodiment, the kit can include strains D1, D2, and/or D3. The kits can additionally include one or more of the exogenous enzymes disclosed herein (for example, one or more of a phytase, a protease, an amylase, a xylanase or a beta-glucanase).

The invention can be further understood by reference to the following examples, which are provided by way of illustration and are not meant to be limiting.

EXAMPLES

Example 1: Materials and Methods

In the following examples, various methods and assays were used as set forth below for case in reading. Any deviations from the protocols provided below are indicated in the relevant sections.

Isolation of *Lactobacillus* strains from chicken intestinal tracts: GIT samples dissected in the field were transferred into anaerobic transport media as quickly as possible. Strain isolation started once intestinal samples arrived at the lab. Ceca, ileum, jejunum or duodenum samples were dissected using sterile technique inside an anaerobic chamber. The digesta was discarded and mucosal-bound material was scraped using a loop. This material was then transferred into sterile media or buffer and serially diluted. Serial dilutions ranging from $10^{-1}$ to $10^{-6}$ were plated onto petri dishes or omni plates of various media types using plating beads. These plates were then incubated anaerobically until colonies became visible. De Man, Rogosa and Sharpe agar (MRS) or Brain heart infusion medium (BHI) was used for isolation.

Once colonies were visible on an agar plate, colonies were picked in the anaerobic chamber to liquid media in a 96 deep well plate. Some plates were initially picked into a small volume of liquid media (i.e. 200 µl) and then media added to 800 µl 1-4 days later to increase growth. Colony picking could be done at multiple time points for the same plate. For example, large colonies were picked on day 2, and then very small colonies or new colonies were picked at day 5.

Analysis of the microbial composition of mucosa region of the small intestines by 16S sequencing and netB qPCR: To evaluate the microbial composition of the small intes-tines, chicken swabs of the mucosa region of the small intestines was analyzed by 16S sequencing. Chicken gastro intestinal tract (GIT) is removed and separated into four sections: duodenum, jejunum, ileum and ceca. Each section is squeezed to remove the digesta contents and then cut longitudinally to expose the inner surface. Each section inner surface is swabbed with a FLOQSwab (Copan Mfgr, Murrieta, CA). The swab is added directly to a well of a 96 well Qiagen MagAttract PowerSoil kit (Qiagen, Hilden, Germany). The swabs were processed for bacterial DNA isolation as per the manufacturer's instructions using the KingFisher Flex automation platform. Isolated metag-enomic DNA is then ready for NGS sample preparation Metagenomic DNA purified from chicken GIT swabs was prepared for 16S community sequencing as follows: DNA is diluted 1:5 by adding 20 µl of molecular biology grade water to 5 µl of purified DNA at 0.1-10 ng/µl. Then 2 µl of the diluted DNA was added to a PCR reaction along with 25 µl of ABI Universal TaqMan Reaction mix without UNG (ThermoFisher #4326614), 0.1 µl each PCR primers at 100 uM and 24.8 µl of Molecular Biology Grade water for a total volume of 50 µl. The PCR primers were the Illumina-V4-515F-RJ: TCGTCGGCAGCGTCAGATGTGTATAAGA-GACAGGTGCCAGCMGCCGCGGTAA and Illumina-V4-806R-RJ: GTCTCGTGGGCTCGGAGATGTGTAT AAGAGACAGGGACTACHVGGGTWTCTAAT were used. The PCR reactions were: 10 min at 95° C. followed by 35 cycles of 95° C. 15 sec+55° C. 30 sec+72° C. for 2 min. Amplified reactions were purified using Ampure XP Mag-netic Beads (Beckman Coulter A63881) as per manufactur-er's instructions using the Agilent Bravo Automated Robotic Workstation. 2 µl of each amplicon pool was then indexed in a second PCR reaction using the same conditions as above with Illumina XT Index Primers (Illumina XT v2.0 #FC-131-2001-2004) for 15 cycles. Indexed amplicons are then pooled and purified with AmPure XP Magnetic Beads on the Agilent Bravo Automated Robotic Workstation. Pooled, indexed amplicons were quantitated using the Kapa Illumina Library Quantification Kit (KAPA #KK4835) as per manu-facturer's instructions. Purified, quantitated, indexed, pools were loaded on the Illumina MiSeq at a final concentration of 8 pM along with 15% Illumina PhiX (Illumina FC-110-3001). Sequencing was run for 2×250 Paired End cycles.

The 16S Amplicon data from Illumina Miseq sequencing were analyzed. Paired-end reads were first merged by Flash (Mogoc et al., *Bioinformatics*. 2011; 27:2957-63). The for-ward and reverse primers were removed from the merged reads, and reads with overall quality score less than 20 were discarded by RDP Initial Process tool (Fish et al., *Front Microbiol*. 2013; 4:291). This step also removes reads originated from chicken mitochondria due to their length shorter than 200 bp. In the next step reads were assigned to bacterial and archaeal taxonomy by RDP Classifier (Wang et al., *Appl Environ Microbiol*. 73 (16): 5261-5267). The reads passed the above quality processing steps were clustered at 98% by CD-HIT (Li & Godzik, *Bioinformatics*, 2006; 22:1658-9) to obtain Operational Taxonomic Units (OTU). The representative sequence from each OTU was assigned to the closest species by RDP pairwise alignment tool (Fish et al., *Front Microbiol*. 2013; 4:291) against a vetted 16S reference database containing mostly 16S genes from type strains and public genomes. The relative abundance of an OTU in a sample was the fraction of reads assigned to that OTU. An OTU was assigned to a species if it has at least 98% identity to that species in the reference database. The average abundance of a species in a consortium in small intestine was calculated as the average relative abundance of that species from DUO, JEJ and ILL samples of each treatment.

The same DNA preparations were also quantified for netB gene using qPCR. NetB is an important virulence factor for *C. perfringens*. Each assay was run using 1.5 µl of DNA along with 10 µl of TaqMan Universal Master Mix, 0.2 µl of 100 uM Forward and Reverse Primers, 0.05 µl of TaqMan Probe, and 9.55 µl Molecular Biology Grade water. The qPCR reaction conditions were as follows: 10 min at 95° C.+40 cycles of 95° C. 15 sec+60° C. 60 sec on the ABI Quant Studio qPCR instrument. Sample data was quantified using genomic DNA from a netB positive *C. perfringens*. Primer and probe sequences used are in Table 5 below.

TABLE 5

| qPCR Primers and Probes | | | |
|---|---|---|---|
| Target | Primer Name | Direc- tion | Sequence (5' to 3') |
| Total Bacteria 16S | 16S-T1- 1369F | for | CGGTGAATA CGTTCYCGG |
| | 16S-T1- 1492R | rev | GGWTACCTT GTTACGACT T |
| | 16S-T1- 1389T | probe | CTTGTACAC ACCGCCCGT C |
| *C. perfringens* | CPerf165F | for | CGCATAACG TTGAAAGAT GG |
| | CPerf269R | rev | CCTTGGTAG GCCGTTACC C |
| | CPerf187T | probe | TCATCATTC AACCAAAGG AGCAATCC |
| netB gene | NetB-RJ- Fwd | Fwd | TGGTGCTGG AATAAATGC TTCAT |
| | NetB-RJ- Rev | Rev | TGCATCATC TTTTCTTTG AATTGTTC |
| | NetB-RJ- MGB | Probe | ATACTATAA GCTATGAAC AACC |

Binding assay to characterize the capability of *Lactobacillus* isolates to attach to mucin and collagen: The major component of the mucus membrane in the small intestines is mucin and the ability to bind to mucin was used to evaluate their ability to adhere to GI track. The binding assay was carried out with 96 wells in a sterile non-TC treated poly-styrene plate. The initial step was the coating of the plate with mucin (type II or type III porcine mucin, Sigma). The mucin solution (1%) was prepared by stirring for a few hours till a homogenous suspension was obtained. The solution was autoclaved before use. 120 µl of mucin solution was added to each 96 well and the plate was incubated at 4° C. overnight. Right before use, the unbound mucin was removed and rinsed twice with 125 µl molecular biology grade water.

For binding assay, fresh overnight cultures grown in MRS medium at 37 or 40° C. were used. The cultures were first collected by centrifugation and washed once with 1×PBS medium. 100 µL culture at 1 OD (600 nm) was added into each well in the washed mucin coated plate and the plate was incubated in the 37° C. anaerobic chamber or anaerobic jar for 2 hours. After incubation, the plate was washed with 100 µL 1×PBS twice and the attached cells in each well was stained by adding 100 µl of 0.1% solution of crystal violet (1% stock solution from Sigma) diluted in water. The plate was allowed to sit for 5 to 10 min at room temperature. The unbound dye was removed and each well was washed three times with 100 µl 1×PBS. To measure the dye bound to the attached cells, 100 µl of 1×PBS was used to re-suspend the bound cells by pipetting up and down. Alternatively, 100 µl of ethanol was used to dissolve the dye. After 20 min, the dye intensity was measured at 570 or 590 nm. The reading reflected the number of attached cells.

A similar procedure was used to evaluate the ability of *Lactobacillus* strains to bind the Biocoat collagen IV plates from Corning. It has been reported that collagen binding is one of the important virulence factors for *C. perfringens* (*Vet Microbiol.* 2015 Nov. 18; 180:299-303). One of the potential beneficial properties of DFM can be the competitive binding of this extracellular matrix.

Antimicrobial assay to characterize *Lactobacillus* isolates for antimicrobial activity against *C. perfringens*: Microplate based antimicrobial assay was performed using supernatants of *Lactobacillus* isolates from chicken GIT samples. Isolates were inoculated in MRS liquid medium and grew at 37° C. for 2 to 3 days anaerobically. Cultures were centrifuged at 4500 rpm for 5 min and supernatants were collected in Costar 96 well plate and filtered. 20 or 25 µL supernatant was used for assay.

The target pathogen *C. perfringens* from a fresh plate was inoculated in BHI medium at 37° C. and grew overnight anaerobically. *C. perfringens* culture was diluted into an OD (600 nm) of 0.1 with BHI medium. 175 or 180 µL diluted *C. perfringens* culture was added to each well containing 20 or 25 µL supernatant to a final volume of 200 µl. For the control, 20 or 25 µL of MRS medium was used. The assay plate was incubated under anaerobic conditions at 37° C. for 18 hours and then OD (600 nm) was measured. The amount of the growth relative to the control was used to measure the antimicrobial activity. Alternatively, the growth was moni-tored continuously using a microtiter reader.

Animal model for necrotic enteritis caused by *C. perfringens*: A challenged diseased model for broiler chicken has been used extensively (*Front Microbiol.* 2016, 7:1416; *J Anim Sci Biotechnol.* 2018, 9:25; *Poult Sci.* 2018 Nov. 18). In this experiment, chickens at day 9 were first challenged with live 1× *Eimeria* vaccine (ADVENT® coccidiosis vac-cine, Huvepharma, Inc., Lincoln, NE 68528). Seventeen (17) birds were in each of the experimental and control groups. The vaccine was diluted in water and each chicken received 1 ml orally. At day 11, each chicken received 1 ml of pathogen cocktail orally. The pathogen cocktail consisted of five *Clostridium perfringens* strains isolated from dis-eased tissues. All strains contained the netB and tpel genes based on the genome analysis. These strains were grown individually in cooked meat medium (Sigma) overnight and the fresh cultures were mixed in equal volume in a glove box to make up the cocktail. The cocktail was used the same day to induce necrotic enteritis.

With this disease model, *Lactobacillus* isolates were evaluated for their efficacy against *C. perfringens* infection. *Lactobacillus* strains were grown in MRS medium under anaerobic conditions. Fresh cultures were mixed in equal volume and the mixed cell suspension for each consortium was aliquoted into serum bottles. The serum bottles were stored at 80° C. and thawed before use. The *Lactobacillus* consortia were fed to each chicken daily by gavage starting at day 1. At day 15, chicken intestines were collected for histopathology analysis and the mucosa samples were used for DNA isolation as described supra.

Example 2: Binding and Antimicrobial Properties of *Lactobacillus* Strains Isolated from Chicken Small Intestines Table 6 summarized the in vitro assay results of *Lactobacillus* strains for their antimicrobial ability and their ability to bind to either mucin or collagen as described per the methods of Example 1. While the activities were strain-dependent, the supernatants from *L.* salivarious isolates had high antimicrobial activity. Those from *L. reuteri* had lower antimicrobial activity, but quite a few had excellent ability to bind to collagen.

TABLE 6

Results of in vitro assays of *Lactobacillus* strains

| Description | Isolates | Mucin Binding[1] | Collagen Binding[1] | Antimicrobial Activity[2] (%) |
|---|---|---|---|---|
| *L. agilis* | H3 | 0.16 | 0.22 | 72 |
| *L. agilis* | A3 | 0.46 | 0.33 | 32 |
| *L. agilis* | D1 | 0.31 | 0.59 | 11 |
| *L. crispatus* | D3 | 0.48 | 0.51 | 45 |
| *L. crispatus* | E3 | 0.98 | 0.58 | 7 |
| *L. gallinarum* | E1 | 0.24 | 0.34 | 0 |
| *L. gallinarum* | H1 | 0.59 | 0.87 | 0 |
| *L. johnsonii* | C3 | 0.43 | 0.54 | 92 |
| *L. reuteri* | E2 | 0.20 | 0.43 | 46 |
| *L. reuteri* | S2 | 0.42 | 0.50 | 8 |
| *L. reuteri* | A2 | 0.85 | 0.72 | 1 |
| *L. reuteri* | S1 | 0.34 | 0.72 | 33 |
| *L. reuteri* | S3 | 0.36 | 0.58 | 6 |
| *L. reuteri* | C1 | 0.59 | 1.04 | 7 |
| *L. salivarius* | D2 | 0.59 | 0.47 | 94 |
| *L. salivarius* | H2 | 0.23 | 0.40 | 94 |
| *L. salivarius* | A1 | 0.33 | 0.34 | 90 |
| *L. salivarius* | C2 | 0.88 | 1.24 | 77 |

[1]The binding activity was measured as OD at 570 nm.
[2]The antimicrobial activity was measured as percent inhibition relative to the control.

Example 3: Animal Model for Necrotic Enteritis Caused by *C. perfringens*

DFM candidates were evaluated for their efficacy against *C. perfringens* infection in an animal model. For animal study, the *lactobacillus* strains were grouped as consortia based on their phylogenetic diversity and representation of a broad spectrum of in vitro assay results. The consortia and their strain composition are listed in Table 7. These strains were grown in MRS medium under anaerobic conditions and the fresh culture were mixed in equal volume inside the glovebox to make up a specific consortium for the animal trial. The mixed cell suspension for each consortium was aliquoted into serum bottles under anaerobic conditions inside a glove box. The serum bottles were stored at 80° C. and thawed before use. Each consortium was fed to chicken daily by gavage starting at day 1. At day 15, chicken intestines were collected for histopathology analysis and the mucosa samples were used for DNA isolation as described in Example 1.

TABLE 7

List of *Lactobacillus* strains used for animal study

| Consortium | Strain 1 | Strain 2 | Strain 3 |
|---|---|---|---|
| A | *L. salivarius* A1 | *L. reuteri* A2 | *L. agilis* A3 |
| C | *L. reuteri* C1 | *L. salivarius* C2 | *L. johnsonii* C3 |
| D | *L. agilis* D1 | *L. salivarius* D2 | *L. crispatus* D3 |

TABLE 7-continued

List of *Lactobacillus* strains used for animal study

| Consortium | Strain 1 | Strain 2 | Strain 3 |
|---|---|---|---|
| E | *L. gallinarum* E1 | *L. reuteri* E2 | *L. crispatus* E3 |
| H | *L. gallinarum* H1 | *L. salivarius* H2 | *L. agilis* H3 |
| S | *L. reuteri* S1 | *L. reuteri* S2 | *L. reuteri* S3 |

The abundance of *C. perfringens* based on 16S analysis using samples from day 15 as described in Example 1 is summarized in Table 8. In the control group (disease model) where no *Lactobacillus* strains were used, necrotic enteritis in the small intestines was observed. Consistent with this result, there was abundance of *C. perfringens* as quantified based on 16S analysis and netB qPCR. Chicken feed with consortia E and C, showed similar high abundance of *C. perfringens* as the chicken in the control group. Chicken from these two groups suffered from necrotic enteritis. This suggests that these two consortia did not show efficacy against the expansion of the pathogen in the animal trial. On the other hand, the abundance of *C. perfringens* was much lower in consortia A, D, H, and S. Histopathology indicated no sign of necrotic enteritis. This result suggests these four consortia had efficacy in the prevention of *C. perfringens* infection. From this animal study, it is clear that the efficacy against *C. perfringens* infection depended on the specific composition of the consortium since both consortia C and E had some of the same *Lactobacillus* species as consortia in A, D, H, and S

TABLE 8

Results of animal trials

| Consortium | CP Abundance[1] | netB qPCR[2] | Necrotic Enteritis |
|---|---|---|---|
| Control | 0.257 | 0.204 | Positive |
| C | 0.349 | 0.335 | Positive |
| E | 0.335 | 0.216 | Positive |
| A | 0.013 | 0.026 | Negative |

US 12,610,970 B2

41

TABLE 8-continued

Results of animal trials

| Consortium | CP Abundance[1] | netB qPCR[2] | Necrotic Enteritis |
|---|---|---|---|
| D | 0.021 | 0.007 | Negative |
| H | 0.001 | 0.001 | Negative |
| S | 0.001 | 0.001 | Negative |

[1]CP Abundance = 16S CP sequence reads/Total 16S Sequence reads (Example 1)
[2]netB qPCR = qPCR netB Copy number/qPCR Total 16S Example 4: Large Scale Animal Trial to Assess Improved Mortality Benefits of Consortium In February 2020, four commercial broiler chicken houses located in the United States were each stocked with approximately 56,000 birds (approximately 224,000 total birds were used in this study). Necrotic enteritis affecting large-scale chicken production in the U.S. is typically most prevalent during the months of November through April.

Each house was divided into two halves; 50% of the birds were supplemented with the Direct Fed Microbial (DFM; a combination of 3 *L. reuteri* strains S1, S2, and S3), the remaining 50% of each house were used as unsupplemented controls. Each half of the house received water via a different waterline. All birds were fed a typical U.S. corn/soy based pelleted feed ad libitum.

Birds were placed on Day 1 and slaughtered on Day 52. The DFM was supplemented into the waterline via the medicator at a dose of $1.2 \times 10^8$ CFU/bird/day on days 17, 18, 19, 20 and 21 of production for three out of 4 houses and day 17 only for one house (day 17 onwards coincides with the highest rate of necrotic enteritis outbreaks typically observed in the field during this time of the year).

Flock mortality data for each of the houses was collected and is shown in The FIGURE Control birds exhibited a combined mortality rate of approximately 11% whereas birds receiving DFM supplementation exhibited mortality rates of 6.9% (i.e. a 61.5% total reduction in mortality over the course of the study).

Survival probability analysis was conducted, and production cost savings were calculated on a per million bird bases. To calculate the cost savings delivered by the DFM supplementation, the following parameters were taken into consideration: weekly mortality, weekly feed consumption, feed cost ($0.11 per lb), chick cost ($0.34 USD per chick), and approximate condemnations. In this study, DFM supplementation and the associated reduction in mortality resulted in avoided losses of approximately $5769 USD or savings of $51,514 USD per million birds.

Example 5: Identification and Removal of Antimicrobial Resistance (AMR) Genes

This Example demonstrates the identification and removal of antimicrobial resistance (AMR) genes from consortia members. AMR genes, particularly those associated with mobile genetic elements, are of concern because they can in some instances be transferred among different bacterial cells, thereby promoting antibiotic resistance. To prevent the spread of these AMR markers and to comply with regulatory requirements, it may be beneficial to remove them from strains used as DFMs in livestock.

The strains from the different consortia were sequenced using a combination of the short-read sequencing technology Illumina and long-read sequencing technology platforms such as Oxford Nanopore Technology or PacBio. The reads from a strain were processed using standard trimming procedures and assembled into a sequence using standard tools such as SPAdes (Bankevich et al,. 2012, *J Comput Biol* 19:455-477), Unicycler (Wick et al., 2017, *PLoS Comput Biol* 13: e1005595), and Pilon (Walker et al., 2014, *PLoS One* 9: e112963). The sequence was subsequently annotated using prokka (Seemann, 2014, *Bioinformatics* 30:2068-2069) or PATRIC (Wattam et al. 2018, *Methods Mol Biol* 1704:79-101). Antimicrobial resistance (AMR) genes were identified using CARD (Alcock et al., 2020, *Nucleic Acids Res* 48: D517-D525), the Comprehensive Antibiotic Resistance Database, and PARTIC (Davis et al., 2016, *Sci Rep* 6:27930). Any AMR genes identified by these databases were subsequently inspected for mobile genetic elements within the surrounding 10 kb.

Strain S3 was found to be free of AMR genes, while S1 and S2 both had two different AMR genes associated with mobile genetic elements: lnuC, a transposon-mediated nucleotidyltransferase, and vatE, a transposon-mediated acetyltransferase. Both genes are next to a transposase. The AMR gene and transposase were found to be flanked by a set of indirect and direct repeats (Achard et al., 2005, *Antimicrob Agents Chemother* 49:2716-2719). Four copies of lnuC spread throughout the genome and one copy of vatE were identified in S1, while one copy of either gene was found in S2. This strain S2 also contained a tetW gene that was not associated with any mobile genetic elements within the surrounding 10 kb of the genes.

Positions of the genes in S1 were identified based on PacBio sequence of lnuC (470,273 forward, 995,196 reverse, 1,149,997 forward, 1,775,176 forward) and vatE (1,439,964) and in S2 based on the ONT sequence of lnuC (161,023 forward), vatE (457,661 forward) and tetW (818,067 reverse).

These genes and their associated transposases are and were removed using standard molecular tools such as recombineering (Zhang et al., 2018, *J Bacteriol* 200; Ozcam et al., 2019, *Appl Environ Microbiol* 85), or CRISPR based methods (Oh & Van Pijkeren, 2014, *Nucleic Acids Res* 42: e131).

We claim:

1. A method for improving one or more metrics in an animal selected from the group consisting of increased bodyweight gain, intestinal health status, decreased feed conversion ratio (FCR), improved gut barrier integrity, reduced mortality, reduced pathogen infection, and reduced pathogen shedding in feces comprising administering an effective amount of a bacterial consortium comprising (a) *Lactobacillus reuteri* strain S1 deposited at Westerdijk Fungal Biodiversity Institute (WFDB) under number CBS 145921 and comprising the 16S ribosomal RNA nucleotide sequence of SEQ ID NO: 7; (b) *Lactobacillus reuteri* strain S2 deposited at WFDB under number CBS 145922 and comprising the 16S ribosomal RNA nucleotide sequence of SEQ ID NO: 8; and (c) *Lactobacillus reuteri* strain S3 deposited at WFDB under number CBS 145923 and comprising the 16S ribosomal RNA nucleotide sequence of SEQ ID NO: 9 to the animal, thereby improving the one or more metrics in the animal, wherein one or more of the bacterial strains in the bacterial consortium further comprise one or more inactivated or deleted antimicrobial resistance (AMR) genes selected from the group consisting of InuC and vatE, and wherein the one or more AMR genes is located within 10 kilobases of a transposon or other mobile genetic element.

2. The method of claim 1, wherein the bacterial consortium increases one or more of the lactate, acetate, isobutyrate, butyrate, isovalerate, and valerate content of the gastrointestinal tract of the animal.

3. The method of claim 1, wherein the pathogen is one or more of *Clostridium perfringens, Campylobacter jejuni*, Enterobacteriaceae, a *Salmonella* sp., and *Escherichia coli*.

4. The method of claim 1, wherein the method further treats, prevents, or decreases incidence of necrotic enteritis.

5. The method of claim 1, wherein the animal is a domesticated bird.

6. The method of claim 5, wherein the domesticated bird is selected from the group consisting of chickens, turkeys, ducks, geese, quail, emus, ostriches, and pheasant.

7. The method of claim 6, wherein the chicken is a broiler or a layer.

8. The method of claim 1, wherein the feed additive composition, the bacterial consortium is administered by water line.

9. The method of claim 1, wherein the consortium produces one or more organic acids selected from the group consisting of lactate, butyrate, isobutyrate, propionate, acetate, isovalerate, and valerate.

10. The method of claim 1, wherein each strain in the bacterial consortium is administered to the animal at a dosage of at least about $1\times10^3$ CFU/day to at least about $1\times10^{15}$ CFU/day.

11. The method of claim 1, wherein the consortium inhibits at least one pathogen selected from avian pathogenic

*Salmonella* sp., *Escherichia coli, Clostridium perfringens* and Enterobacteriaceae in a gastrointestinal tract of a bird having ingested an effective amount of said consortium.

* * * * *

SEQUENCE LISTING

<160> NUMBER OF SEQ ID NOS: 12

<210> SEQ ID NO 1
<211> LENGTH: 1560
<212> TYPE: DNA
<213> ORGANISM: Lactobacillus agilis

<400> SEQUENCE: 1
aatgagagtt tgatcctggc tcaggacgaa cgctggcggc gtgcctaata catgcaagtc      60

```
gaacgctttt ttcaatcatc gtagcttgct acaccgattg aaaattgagt ggcgaacggg      120
tgagtaacac gtgggtaacc tgcccaaaag agggggataa cacttggaaa caggtgctaa      180
taccgcataa ccatgatgac cgcatggtca ttatgtaaaa gatggtttcg gctatcactt      240
ttggatggac ccgcggcgta ttaacttgtt ggtggggtaa cggcctacca aggtaatgat      300
acgtagccga actgagaggt tgatcggcca cattgggact gagacacggc ccaaactcct      360
acgggaggca gcagtaggga atcttccaca atgggcgcaa gcctgatgga gcaacgccgc      420
gtgagtgaag aaggtcttcg gatcgtaaaa ctctgttgtt agagaagaac atgcgagaga      480
gtaactgttc ttgtattgac ggtatctaac cagaaagcca cggctaacta cgtgccagca      540
gccgcggtaa tacgtaggtg gcaagcgttg tccggattta ttgggcgtaa agggaacgca      600
ggcggtcctt taagtctgat gtgaaagcct tcggcttaac cgaagaattg cattggaaac      660
tggaggactt gagtgcagaa gaggagagtg gaactccatg tgtagcggtg aaatgcgtag      720
atatatggaa gaacaccagt ggcgaaagcg gctctctggt ctgtaactga cgctgaggtt      780
cgaaagtgtg ggtagcaaac aggattagat accctggtag tccacaccgt aaacgatgaa      840
tgctaagtgt tggagggttt ccgcccttca gtgctgcagc taacgcaata agcattccgc      900
ctggggagta cgaccgcaag gttgaaactc aaaggaattg acggggggcc gcacaagcgg      960
tggagcatgt ggtttaattc gaagcaacgc gaagaacctt accaggtctt gacatctttt      1020
gaccatctta gagataagat tttcccttcg gggacaaaat gacaggtggt gcatggctgt      1080
cgtcagctcg tgtcgtgaga tgttgggtta agtcccgcaa cgagcgcaac ccttgttgtc      1140
agttgccagc attaagttgg gcactctggc gagactgccg gtgacaaacc ggaggaaggt      1200
ggggacgacg tcaagtcatc atgcccctta tgacctgggc tacacacgtg ctacaatgga      1260
cggtacaacg agtcgcaaac tcgcgagggc aagctaatct cttaaagccg ttctcagttc      1320
ggattgtagg ctgcaactcg cctacatgaa gtcggaatcg ctagtaatcg cgaatcagca      1380
tgtcgcggtg aatacgttcc cgggccttgt acacaccgcc cgtcacacca tgagagtttg      1440
taacacccaa agccggtggg gtaacctttt aggagctagc cgtctaaggt gggacagatg      1500
attggggtga gtcgtaaca aggtagccgt aggagaacct gcggctggat cacctccttt       1560
```

<210> SEQ ID NO 2
<211> LENGTH: 1559
<212> TYPE: DNA
<213> ORGANISM: Lactobacillus salivarius

<400> SEQUENCE: 2

```
aatgagagtt tgatcctggc tcaggacgaa cgctggcggc gtgcctaata catgcaagtc       60
gaacgaaact ttcttacacc gaatgcttgc attcaccgta agaagttgag tggcggacgg      120
gtgagtaaca cgtgggtaac ctgcctaaaa gaaggggata acacttggaa acaggtgcta      180
ataccgtata tctctaagga tcgcatgatc cttagatgaa agatggttct gctatcgctt      240
ttagatggac ccgcggcgta ttaactagtt ggtggggtaa cggcctacca aggtgatgat      300
acgtagccga actgagaggt tgatcggcca cattgggact gagacacggc ccaaactcct      360
acgggaggca gcagtaggga atcttccaca atgggcgcaa gtctgatgga gcaacgccgc      420
gtgagtgaag aaggtcttcg gatcgtaaaa ctctgttgtt agagaagaac acgagtgaga      480
gtaactgttc attcgatgac ggtatctaac cagcaagtca cggctaacta cgtgccagca      540
gccgcggtaa tacgtaggtg gcaagcgttg tccggattta ttgggcgtaa agggaacgca      600
ggcggtcttt taagtctgat gtgaaagcct tcggcttaac cggagtagtg cattggaaac      660
```

-continued

```
tggaagactt gagtgcagaa gaggagagtg gaactccatg tgtagcggtg aaatgcgtag      720
atatatggaa gaacaccagt ggcgaaagcg gctctctggt ctgtaactga cgctgaggtt      780
cgaaagcgtg ggtagcaaac aggattagat accctggtag tccacgccgt aaacgatgaa      840
tgctaggtgt tggagggttt ccgcccttca gtgccgcagc taacgcaata agcattccgc      900
ctggggagta cgaccgcaag gttgaaactc aaaggaattg acggggcccc gcacaagcgg      960
tggagcatgt ggtttaattc gaagcaacgc gaagaacctt accaggtctt gacatccttt     1020
gaccacctaa gagattaggc tttcccttcg gggacaaagt gacaggtggt gcatggctgt     1080
cgtcagctcg tgtcgtgaga tgttgggtta agtcccgcaa cgagcgcaac ccttgttgtc     1140
agttgccagc attaagttgg gcactctggc gagactgccg gtgacaaacc ggaggaaggt     1200
ggggacgacg tcaagtcatc atgcccctta tgacctgggc tacacacgtg ctacaatgga     1260
cggtacaacg agtcgcaaga ccgcgaggtt tagctaatct cttaaagccg ttctcagttc     1320
ggattgtagg ctgcaactcg cctacatgaa gtcggaatcg ctagtaatcg cgaatcagca     1380
tgtcgcggtg aatacgttcc cgggccttgt acacaccgcc cgtcacacca tgagagtttg     1440
taacacccaa agccggtggg gtaaccgcaa ggagccagcc gtctaaggtg gacagatga     1500 ttggggtgaa gtcgtaacaa ggtagccgta ggagaacctg cggctggatc acctcctttt    1559
```

<210> SEQ ID NO 3
<211> LENGTH: 1560
<212> TYPE: DNA
<213> ORGANISM: Lactobacillus agilis

<400> SEQUENCE: 3

```
aatgagagtt tgatcctggc tcaggacgaa cgctggcggc gtgcctaata catgcaagtc       60
gaacgctttt ttcaatcatc gtagcttgct acaccgattg aaaattgagt ggcgaacggg      120
tgagtaacac gtgggtaacc tgcccaaaag aggggggataa cacttggaaa caggtgctaa      180
taccgcataa ccatgatgac cgcatggtca ttatgtaaaa gatggtttcg gctatcactt      240
ttggatggac ccgcggcgta ttaacttgtt ggtggggtaa cggcctacca aggtaatgat      300
acgtagccga actgagaggt tgatcggcca cattgggact gagacacggc ccaaactcct      360
acgggaggca gcagtaggga atcttccaca atgggcgcaa gcctgatgga gcaacgccgc      420
gtgagtgaag aaggtcttcg gatcgtaaaa ctctgttgtt agagaagaac atgcaggaga      480
gtaactgttc ttgtattgac ggtatctaac cagaaagcca cggctaacta cgtgccagca      540
gccgcggtaa tacgtaggtg gcaagcgttg tccggattta ttgggcgtaa agggaacgca      600
ggcggtcctt taagtctgat gtgaaagcct tcggcttaac cgaagaattg cattggaaac      660
tggaggactt gagtgcagaa gaggagagtg gaactccatg tgtagcggtg aaatgcgtag      720
atatatggaa gaacaccagt ggcgaaagcg gctctctggt ctgtaactga cgctgaggtt      780
cgaaagtgtg ggtagcaaac aggattagat accctggtag tccacaccgt aaacgatgaa      840
tgctaagtgt tggagggttt ccgcccttca gtgctgcagc taacgcaata agcattccgc      900
ctggggagta cgaccgcaag gttgaaactc aaaggaattg acggggcccc gcacaagcgg      960
tggagcatgt ggtttaattc gaagcaacgc gaagaacctt accaggtctt gacatctttt     1020
gaccatctta gagataagat tttcccttcg gggacaaaat gacaggtggt gcatggctgt     1080
cgtcagctcg tgtcgtgaga tgttgggtta agtcccgcaa cgagcgcaac ccttgttgtc     1140
agttgccagc attaagttgg gcactctggc gagactgccg gtgacaaacc ggaggaaggt     1200
```

```
ggggacgacg tcaagtcatc atgcccctta tgacctgggc tacacacgtg ctacaatgga    1260
cggtacaacg agtcgcaaac tcgcgagggc aagctaatct cttaaagccg ttctcagttc    1320
ggattgtagg ctgcaactcg cctacatgaa gtcggaatcg ctagtaatcg cgaatcagca    1380
tgtcgcggtg aatacgttcc cgggccttgt acacaccgcc cgtcacacca tgagagtttg    1440
taacacccaa agccggtggg gtaacctttt aggagctagc cgtctaaggt gggacagatg    1500
attggggtga agtcgtaaca aggtagccgt aggagaacct gcggctggat cacctccttt    1560
```

```
<210> SEQ ID NO 4
<211> LENGTH: 1559
<212> TYPE: DNA
<213> ORGANISM: Lactobacillus salivarius

<400> SEQUENCE: 4
aatgagagtt tgatcctggc tcaggacgaa cgctggcggc gtgcctaata catgcaagtc      60
gaacgaaact ttcttacacc gaatgcttgc attcaccgta agaagttgag tggcggacgg     120
gtgagtaaca cgtgggtaac ctgcctaaaa gaaggggata cacttggaa acaggtgcta     180 ataccgtata tctctaagga tcgcatgatc cttagatgaa agatggttct gctatcgctt     240
ttagatggac ccgcggcgta ttaactagtt ggtggggtaa cggcctacca aggtgatgat     300
acgtagccga actgagaggt tgatcggcca cattgggact gagacacggc ccaaactcct     360
acgggaggca gcagtaggga atcttccaca atggacgcaa gtctgatgga caacgccgc     420 gtgagtgaag aaggtcttcg gatcgtaaaa ctctgttgtt agagaagaac acgagtgaga     480
gtaactgttc attcgatgac ggtatctaac cagcaagtca cggctaacta cgtgccagca     540
gccgcggtaa tacgtaggtg gcaagcgttg tccggattta ttgggcgtaa agggaacgca     600
ggcggtcttt taagtctgat gtgaaagcct tcggcttaac cggagtagtg cattggaaac     660
tggaagactt gagtgcagaa gaggagagtg gaactccatg tgtagcggtg aaatgcgtag     720
atatatggaa gaacaccagt ggcgaaagcg gctctctggt ctgtaactga cgctgaggtt     780
cgaaagcgtg ggtagcaaac aggattagat accctggtag tccacgccgt aaacgatgaa     840
tgctaggtgt tggagggttt ccgcccttca gtgccgcagc taacgcaata agcattccgc     900
ctggggagta cgaccgcaag gttgaaactc aaaggaattg acggggggccc gcacaagcgg     960 tggagcatgt ggtttaattc gaagcaacgc gaagaacctt accaggtctt gacatccttt    1020
gaccacctaa gagattaggc tttcccttcg gggacaaagt gacaggtggt gcatggctgt    1080
cgtcagctcg tgtcgtgaga tgttgggtta agtcccgcaa cgagcgcaac ccttgttgtc    1140
agttgccagc attaagttgg gcactctggc gagactgccg gtgacaaacc ggaggaaggt    1200
ggggacgacg tcaagtcatc atgcccctta tgacctgggc tacacacgtg ctacaatgga    1260
cggtacaacg agtcgcaaga ccgcgaggtt tagctaatct cttaaagccg ttctcagttc    1320
ggattgtagg ctgcaactcg cctacatgaa gtcggaatcg ctagtaatcg cgaatcagca    1380
tgtcgcggtg aatacgttcc cgggccttgt acacaccgcc cgtcacacca tgagagtttg    1440
taacacccaa agccggtggg gtaaccgcaa ggagccagcc gtctaaggtg ggacagatga    1500
ttggggtgaa gtcgtaacaa ggtagccgta ggagaacctg cggctggatc acctccttt    1559
```

```
<210> SEQ ID NO 5
<211> LENGTH: 1560
<212> TYPE: DNA
<213> ORGANISM: Lactobacillus agilis

<400> SEQUENCE: 5
```

```
aatgagagtt tgatcctggc tcaggacgaa cgctggcggc gtgcctaata catgcaagtc      60
gaacgctttt ttcaatcatc gtagcttgct acaccgattg aaaattgagt ggcgaacggg     120
tgagtaacac gtgggtaacc tgcccaaaag aggggaataa cacttggaaa caggtgctaa     180
taccgcataa ccatgatgac cgcatggtca ttatgtaaaa gatggtttcg gctatcactt     240
ttggatggac ccgcggcgta ttaacttgtt ggtggggtaa cggcctacca aggtaatgat     300
acgtagccga actgagaggt tgatcggcca cattgggact gagacacggc ccaaactcct     360
acgggaggca gcagtaggga atcttccaca atgggcgcaa gcctgatgga gcaacgccgc     420
gtgagtgaag aaggtcttcg gatcgtaaaa ctctgttgtt agagaagaac atgcaggaga     480
gtaactgttc ttgtattgac ggtatctaac agaaagcca cggctaacta cgtgccagca      540
gccgcggtaa tacgtaggtg gcaagcgttg tccggattta ttgggcgtaa agggaacgca     600
ggcggtcctt taagtctgat gtgaaagcct tcggcttaac cgaagaattg cattggaaac     660
tggaggactt gagtgcagaa gaggagagtg gaactccatg tgtagcggtg aaatgcgtag     720
atatatggaa gaacaccagt ggcgaaagcg gctctctggt ctgtaactga cgctgaggtt     780
cgaaagtgtg ggtagcaaac aggattagat accctggtag tccacaccgt aaacgatgaa     840
tgctaagtgt tggagggttt ccgcccttca gtgctgcagc taacgcaata agcattccgc     900
ctggggagta cgaccgcaag gttgaaactc aaaggaattg acgggggccc gcacaagcgg     960
tggagcatgt ggtttaattc gaagcaacgc gaagaacctt accaggtctt gacatctttt    1020
gaccatctta gagataagat tttccttcg gggacaaaat gacaggtggt gcatggctgt     1080
cgtcagctcg tgtcgtgaga tgttgggtta agtcccgcaa cgagcgcaac ccttgttgtc    1140
agttgccagc attaagttgg gcactctggc gagactgccg gtgacaaacc ggaggaaggt    1200
ggggacgacg tcaagtcatc atgccccctta tgacctgggc tacacacgtg ctacaatgga    1260
cggtacaacg agtcgcaaac tcgcgagggc aagctaatct cttaaagccg ttctcagttc    1320
ggattgtagg ctgcaactcg cctacatgaa gtcggaatcg ctagtaatcg cgaatcagca    1380
tgtcgcggtg aatacgttcc cgggccttgt acacaccgcc cgtcacacca tgagagtttg    1440
taacacccaa agccggtggg gtaacctttt aggagctagc cgtctaaggt gggacagatg    1500
attggggtga agtcgtaaca aggtagccgt aggagaacct gcggctggat cacctccttt    1560
```

```
<210> SEQ ID NO 6
<211> LENGTH: 1561
<212> TYPE: DNA
<213> ORGANISM: Lactobacillus crispatus

<400> SEQUENCE: 6
```

```
aatgagagtt tgatcctggc tcaggacgaa cgctggcggc gtgcctaata catgcaagtc      60
gagcgagcgg aactaacaga tttacttcgg taatgacgtt aggaaagcga gcggcggatg     120
ggtgagtaac acgtggggaa cctgccccat agtctgggat accacttgga aacaggtgct     180
aataccggat aagaaagcag atcgcatgat cagcttttaa aaggcggcgt aagctgtcgc     240
tatgggatgg ccccgcggtg cattagctag ttggtaaggt aaaggcttac caaggcgatg     300
atgcatagcc gagttgagag actgatcggc cacattggga ctgagacacg gcccaaactc     360
ctacgggagg cagcagtagg gaatcttcca caatggacgc aagtctgatg gagcaacgcc     420
gcgtgagtga agaaggtttt cggatcgtaa agctctgttg ttggtgaaga aggatagagg     480
tagtaactgg ccttatttg acggtaatca accagaaagt cacggctaac tacgtgccag      540
```

-continued

```
cagccgcggt aatacgtagg tggcaagcgt tgtccggatt tattgggcgt aaagcgagcg      600
caggcggaag aataagtctg atgtgaaagc cctcggctta accgaggaac tgcatcggaa      660
actgtttttc ttgagtgcag aagaggagag tggaactcca tgtgtagcgg tggaatgcgt      720
agatatatgg aagaacacca gtggcgaagg cggctctctg gtctgcaact gacgctgagg      780
ctcgaaagca tgggtagcga acaggattag ataccctggt agtccatgcc gtaaacgatg      840
agtgctaagt gttgggaggt ttccgcctct cagtgctgca gctaacgcat taagcactcc      900
gcctggggag tacgaccgca aggttgaaac tcaaaggaat tgacgggggc ccgcacaagc      960
ggtggagcat gtggtttaat tcgaagcaac gcgaagaacc ttaccaggtc ttgacatcta     1020
gtgccatttg tagagataca aagttccctt cggggacgct aagacaggtg gtgcatggct     1080
gtcgtcagct cgtgtcgtga gatgttgggt taagtcccgc aacgagcgca acccttgtta     1140
ttagttgcca gcattaagtt gggcactcta atgagactgc cggtgacaaa ccggaggaag     1200
gtggggatga cgtcaagtca tcatgcccct tatgacctgg gctacacacg tgctacaatg     1260
ggcagtacaa cgagaagcga gcctgcgaag gcaagcgaat ctctgaaagc tgttctcagt     1320
tcggactgca gtctgcaact cgactgcacg aagctggaat cgctagtaat cgcggatcag     1380
cacgccgcgg tgaatacgtt cccgggcctt gtacacaccg cccgtcacac catgggagtc     1440
tgcaatgccc aaagccggtg gcctaacctt cgggaaggag ccgtctaagg cagggcagat     1500
gactggggtg aagtcgtaac aaggtagccg taggagaacc tgcggctgga tcacctcctt     1560
t                                                                     1561
```

```
<210> SEQ ID NO 7
<211> LENGTH: 1065
<212> TYPE: DNA
<213> ORGANISM: Lactobacillus reuteri

<400> SEQUENCE: 7
```

```
gtgacggtat ccaaccagaa agtcacggct aactacgtgc cagcagccgc ggtaatacgt       60
aggtggcaag cgttatccgg atttattggg cgtaaagcga gcgcaggcgg ttgcttaggt      120
ctgatgtgaa agccttcggc ttaaccgaag aagtgcatcg gaaaccgggc gacttgagtg      180
cagaagagga cagtggaact ccatgtgtag cggtggaatg cgtagatata tggaagaaca      240
ccagtggcga aggcggctgt ctggtctgca actgacgctg aggctcgaaa gcatgggtag      300
cgaacaggat tagataccct ggtagtccat gccgtaaacg atgagtgcta ggtgttggag      360
ggtttccgcc cttcagtgcc ggagctaacg cattaagcac tccgcctggg gagtacgacc      420
gcaaggttga aactcaaagg aattgacggg ggcccgcaca agcggtggag catgtggttt      480
aattcgaagc tacgcgaaga accttaccag gtcttgacat cttgcgctaa ccttagagat      540
aaggcgttcc cttcggggac gcaatgacag gtggtgcatg gtcgtcgtca gctcgtgtcg      600
tgagatgttg ggttaagtcc cgcaacgagc gcaacccttg ttactagttg ccagcattaa      660
gttgggcact ctagtgagac tgccggtgac aaaccggagg aaggtgggga cgacgtcaga      720
tcatcatgcc ccttatgacc tgggctacac acgtgctaca atggacggta caacgagtcg      780
caagctcgcg agagtaagct aatctcttaa agccgttctc agttcggact gtaggctgca      840
actcgcctac acgaagtcgg aatcgctagt aatcgcggat cagcatgccg cggtgaatac      900
gttcccgggc cttgtacaca ccgcccgtca ccatgggagt ttgtaacg cccaaagtcg      960 gtggcctaac ctttatggag ggagccgcct aaggcgggac agatgactgg ggtgaagtcg     1020
taacaaggta gccgtaggag aacctgcggc tggatcacct ccttt                     1065
```

```
<210> SEQ ID NO 8
<211> LENGTH: 1065
<212> TYPE: DNA
<213> ORGANISM: Lactobacillus reuteri

<400> SEQUENCE: 8
gtgacggtat ccaaccagaa agtcacggct aactacgtgc cagcagccgc ggtaatacgt      60
aggtggcaag cgttatccgg atttattggg cgtaaagcga gcgcaggcgg ttgcttaggt     120
ctgatgtgaa agccttcggc ttaaccgaag aagtgcatcg gaaaccgggc gacttgagtg     180
cagaagagga cagtggaact ccatgtgtag cggtggaatg cgtagatata tggaagaaca     240
ccagtggcga aggcggctgt ctggtctgca actgacgctg aggctcgaaa gcatgggtag     300
cgaacaggat tagataccct ggtagtccat gccgtaaacg atgagtgcta ggtgttggag     360
ggtttccgcc cttcagtgcc ggagctaacg cattaagcac tccgcctggg gagtacgacc     420
gcaaggttga aactcaaagg aattgacggg ggcccgcaca agcggtggag catgtggttt     480
aattcgaagc tacgcgaaga accttaccag gtcttgacat cttgcgctaa ccttagagat     540
aaggcgttcc cttcggggac gcaatgacag gtggtgcatg gtcgtcgtca gctcgtgtcg     600
tgagatgttg ggttaagtcc cgcaacgagc gcaacccttg ttactagttg ccagcattaa     660
gttgggcact ctagtgagac tgccggtgac aaaccggagg aaggtgggga cgacgtcaga     720
tcatcatgcc ccttatgacc tgggctacac acgtgctaca atggacggta caacgagtcg     780
caagctcgcg agagtaagct aatctcttaa agccgttctc agttcggact gtaggctgca     840
actcgcctac acgaagtcgg aatcgctagt aatcgcggat cagcatgccg cggtgaatac     900
gttcccgggc cttgtacaca ccgcccgtca caccatggga gtttgtaacg cccaaagtcg     960
gtggcctaac ctttatggag ggagccgcct aaggcgggac agatgactgg ggtgaagtcg    1020
taacaaggta gccgtaggag aacctgcggc tggatcacct ccttt                    1065

<210> SEQ ID NO 9
<211> LENGTH: 1350
<212> TYPE: DNA
<213> ORGANISM: Lactobacillus reuteri

<400> SEQUENCE: 9
ttgtttgaaa gatggctttg gctatcactc tgggatggac ctgcggtgca ttagctagtt      60
ggtaaggtaa cggcttacca aggcgatgat gcatagccga gttgagagac tgatcggcca     120
caatggaact gagacacggt ccatactcct acgggaggca gcagtaggga atcttccaca     180
atgggcgcaa gcctgatgga gcaacaccgc gtgagtgaag aagggtttcg gctcgtaaag     240
ctctgttgtt ggagaagaac gtgcgtgaga gtaactgttc acgcagtgac ggtatccaac     300
cagaaagtca cggctaacta cgtgccagca gccgcggtaa tacgtaggtg gcaagcgtta     360
tccggattta ttgggcgtaa agcgagcgca ggcggttgct taggtctgat gtgaaagcct     420
tcggcttaac cgaagaagtg catcggaaac cgggcgactt gagtgcagaa gaggacagtg     480
gaactccatg tgtagcggtg gaatgcgtag atatatggaa gaacaccagt ggcgaaggcg     540
gctgtctggt ctgcaactga cgctgaggct cgaaagcatg ggtagcgaac aggattagat     600
accctggtag tccatgccgt aaacgatgag tgctaggtgt tggagggttt ccgcccttca     660
gtgccggagc taacgcatta agcactccgc ctggggagta cgaccgcaag gttgaaactc     720
aaaggaattg acggggcccc gcacaagcgg tggagcatgt ggtttaattc gaagctacgc     780
```

-continued

```
gaagaacctt accaggtctt gacatcttgc gctaacctta gagataaggc gttcccttcg      840
gggacgcaat gacaggtggt gcatggtcgt cgtcagctcg tgtcgtgaga tgttgggtta      900
agtcccgcaa cgagcgcaac ccttgttact agttgccagc attaagttgg gcactctagt      960
gagactgccg gtgacaaacc ggaggaaggt ggggacgacg tcagatcatc atgcccctta     1020
tgacctgggc tacacacgtg ctacaatgga cggtacaacg agtcgcaagc tcgcgagagt     1080
aagctaatct cttaaagccg ttctcagttc ggactgtagg ctgcaactcg cctacacgaa     1140
gtcggaatcg ctagtaatcg cggatcagca tgccgcggtg aatacgttcc cgggccttgt     1200
acacaccgcc cgtcacacca tgggagtttg taacgcccaa agtcggtggc ctaaccttta     1260
tggagggagc cgcctaaggc gggacagatg actgggggtga agtcgtaaca aggtagccgt     1320
aggagaacct gcggctggat cacctccttt                                      1350
```

<210> SEQ ID NO 10
<211> LENGTH: 1559
<212> TYPE: DNA
<213> ORGANISM: Lactobacillus salivarius

<400> SEQUENCE: 10

```
aatgagagtt tgatcctggc tcaggacgaa cgctggcggc gtgcctaata catgcaagtc       60
gaacgaaact ttcttacacc gaatgcttgc attcaccgta agaagttgag tggcggacgg      120
gtgagtaaca cgtgggtaac ctgcctaaaa gaaggggata cacttggaa acaggtgcta      180 ataccgtata tctctaagga tcgcatgatc cttagatgaa agatggttct gctatcgctt      240
ttagatggac ccgcggcgta ttaactagtt ggtggggta a cggcctacca aggtgatgat      300
acgtagccga actgagaggt tgatcggcca cattgggact gagacacggc ccaaactcct      360
acgggaggca gcagtaggga atcttccaca atggacgcaa gtctgatgga gcaacgccgc      420
gtgagtgaag aaggtcttcg gatcgtaaaa ctctgttgtt agagaagaac acgagtgaga      480
gtaactgttc attcgatgac ggtatctaac cagcaagtca cggctaacta cgtgccagca      540
gccgcggtaa tacgtaggtg gcaagcgttg tccggattta ttgggcgtaa agggaacgca      600
ggcggtcttt taagtctgat gtgaaagcct tcggcttaac cggagtagtg cattggaaac      660
tggaagactt gagtgcagaa gaggagagtg gaactccatg tgtagcggtg aaatgcgtag      720
atatatggaa gaacaccagt ggcgaaagcg gctctctggt ctgtaactga cgctgaggtt      780
cgaaagcgtg ggtagcaaac aggattagat accctggtag tccacgccgt aaacgatgaa      840
tgctaggtgt tggagggttt ccgcccttca gtgccgcagc taacgcaata agcattccgc      900
ctggggagta cgaccgcaag gttgaaactc aaaggaattg acgggggccc gcacaagcgg      960
tggagcatgt ggtttaattc gaagcaacgc gaagaacctt accaggtctt gacatccttt     1020
gaccacctaa gagattaggc tttcccttcg gggacaaagt gacaggtggt gcatggctgt     1080
cgtcagctcg tgtcgtgaga tgttgggtta agtcccgcaa cgagcgcaac ccttgttgtc     1140
agttgccagc attaagttgg gcactctggc gagactgccg gtgacaaacc ggaggaaggt     1200
ggggacgacg tcaagtcatc atgcccctta tgacctgggc tacacacgtg ctacaatgga     1260
cggtacaacg agtcgcaaga ccgcgaggtt tagctaatct cttaaagccg ttctcagttc     1320
ggattgtagg ctgcaactcg cctacatgaa gtcggaatcg ctagtaatcg cgaatcagca     1380
tgtcgcggtg aatacgttcc cgggccttgt acacaccgcc cgtcacacca tgagagtttg     1440
taacacccaa agccgtgggg gtaaccgcaa ggagccagcc gtctaaggtg ggacagatga     1500
ttggggtgaa gtcgtaacaa ggtagccgta ggagaacctg cggctggatc acctccttt      1559
```

-continued

```
<210> SEQ ID NO 11
<211> LENGTH: 1561
<212> TYPE: DNA
<213> ORGANISM: Lactobacillus gallinarum

<400> SEQUENCE: 11
aatgagagtt tgatcctggc tcaggacgaa cgctggcggc gtgcctaata catgcaagtc      60
gagcgagcag aaccagcaga tttacttcgg taatgacgct ggggacgcga gcggcggatg     120
ggtgagtaac acgtggggaa cctgccccat agtctgggat accacttgga aacaggtgct     180
aataccggat aagaaagcag atcgcatgat cagcttataa aaggcggcgt aagctgtcgc     240
tatgggatgg ccccgcggtg cattagctag ttggtaaggt aacggcttac caaggcgatg     300
atgcatagcc gagttgagag actgatcggc cacattggga ctgagacacg gcccaaactc     360
ctacgggagg cagcagtagg gaatcttcca caatggacgc aagtctgatg gagcaacgcc     420
gcgtgagtga agaaggtttt cggatcgtaa agctctgttg ttggtgaaga aggatagagg     480
tagtaactgg cctttatttg acggtaatca accagaaagt cacggctaac tacgtgccag     540
cagccgcggt aatacgtagg tggcaagcgt tgtccggatt tattgggcgt aaagcgagcg     600
caggcggaaa aataagtctg atgtgaaagc cctcggctta accgaggaac tgcatcggaa     660
actgtttttc ttgagtgcag aagaggagag tggaactcca tgtgtagcgg tggaatgcgt     720
agatatatgg aagaacacca gtggcgaagg cggctctctg gtctgcaact gacgctgagg     780
ctcgaaagca tgggtagcga acaggattag ataccctggt agtccatgcc gtaaacgatg     840
agtgctaagt gttgggaggt ttccgcctct cagtgctgca gctaacgcat taagcactcc     900
gcctggggag tacgaccgca aggttgaaac tcaaaggaat tgacgggggc cgcacaagc     960 ggtggagcat gtggtttaat tcgaagcaac gcgaagaacc ttaccaggtc ttgacatcta    1020
gtgccatcct aagagattag gagttccctt cggggacgct aagacaggtg gtgcatggct    1080
gtcgtcagct cgtgtcgtga gatgttgggt taagtcccgc aacgagcgca acccttgtta    1140
ttagttgcca gcattaagtt gggcactcta atgagactgc cggtgacaaa ccggaggaag    1200
gtggggatga cgtcaagtca tcatgcccct tatgacctgg gctacacacg tgctacaatg    1260
ggcagtacaa cgagaagcga gcctgcgaag gcaagcgaat ctctgaaagc tgttctcagt    1320
tcggactgca gtctgcaact cgactgcacg aagctggaat cgctagtaat cgcggatcag    1380
cacgccgcgg tgaatacgtt cccgggcctt gtacacaccg cccgtcacac catggaagtc    1440
tgcaatgccc aaagccggtg gcctaacctt cgggaaggag ccgtctaagg cagggcagat    1500
gactggggtg aagtcgtaac aaggtagccg taggagaacc tgcggctgga tcacctcctt    1560
t                                                                    1561

<210> SEQ ID NO 12
<211> LENGTH: 1573
<212> TYPE: DNA
<213> ORGANISM: Lactobacillus reuteri

<400> SEQUENCE: 12
tatgagagtt tgatcctggc tcaggatgaa cgccggcggt gtgcctaata catgcaagtc      60
gtacgcactg gcccaactga ttgatggtgc ttgcacctga ttgacgatgg atcaccagtg     120
agtggcggac gggtgagtaa cacgtaggta acctgccccg gagcggggga taacatttgg     180
aaacagatgc taataccgca taacaacaaa agccacatgg cttttgtttg aaagatggct     240
```

US 12,610,970 B2

59                                                                                              60

-continued

```
ttggctatca ctctgggatg gacctgcggt gcattagcta gttggtaagg taacggctta      300
ccaaggcgat gatgcatagc cgagttgaga gactgatcgg ccacaatgga actgagacac      360
ggtccatact cctacgggag gcagcagtag ggaatcttcc acaatgggcg caagcctgat      420
ggagcaacac cgcgtgagtg aagaagggtt tcggctcgta aagctctgtt gttggagaag      480
aacgtgcgtg agagtaactg ttcacgcagt gacggtatcc aaccagaaag tcacggctaa      540
ctacgtgcca gcagccgcgg taatacgtag gtggcaagcg ttatccggat ttattgggcg      600
taaagcgagc gcaggcggtt gcttaggtct gatgtgaaag ccttcggctt aaccgaagaa      660
gtgcatcgga aaccgggcga cttgagtgca gaagaggaca gtggaactcc atgtgtagcg      720
gtggaatgcg tagatatatg gaagaacacc agtggcgaag gcggctgtct ggtctgcaac      780
tgacgctgag gctcgaaagc atgggtagcg aacaggatta gataccctgg tagtccatgc      840
cgtaaacgat gagtgctagg tgttggaggg tttccgccct tcagtgccgg agctaacgca      900
ttaagcactc cgcctgggga gtacgaccgc aaggttgaaa ctcaaaggaa ttgacggggg      960
cccgcacaag cggtggagca tgtggtttaa ttcgaagcta cgcgaagaac cttaccaggt     1020
cttgacatct tgcgctaacc ttagagataa ggcgttccct tcggggacgc aatgacaggt     1080
ggtgcatggt cgtcgtcagc tcgtgtcgtg agatgttggg ttaagtcccg caacgagcgc     1140
aacccttgtt actagttgcc agcattaagt tgggcactct agtgagactg ccggtgacaa     1200
accggaggaa ggtggggacg acgtcagatc atcatgcccc ttatgacctg ggctacacac     1260
gtgctacaat ggacggtaca acgagtcgca agctcgcgag agtaagctaa tctcttaaag     1320
ccgttctcag ttcggactgt aggctgcaac tcgcctacac gaagtcggaa tcgctagtaa     1380
tcgcggatca gcatgccgcg gtgaatacgt tcccgggcct tgtacacacc gcccgtcaca     1440
ccatgggagt ttgtaacgcc caaagtcggt ggcctaacct ttatggaggg agccgcctaa     1500
ggcgggacag atgactgggg tgaagtcgta acaaggtagc cgtaggagaa cctgcggctg     1560
gatcacctcc ttt                                                       1573
```